United States Patent [19]

Makisumi et al.

[11] 4,256,640
[45] Mar. 17, 1981

[54] TETRAHYDROTHIOPYRANO[2,3-b]INDOLE DERIVATIVES

[75] Inventors: Yasuo Makisumi; Susumu Takada, both of Kawanishi; Takashi Sasatani; Natsuki Ishizuka, both of Sakai, all of Japan

[73] Assignee: Shionogi & Co., Ltd., Osaka, Japan

[21] Appl. No.: 39,382

[22] Filed: May 15, 1979

[30] Foreign Application Priority Data

May 23, 1978 [JP] Japan .................................. 53-61832

[51] Int. Cl.³ .............................................. C07D 573/14
[52] U.S. Cl. ...................... 260/326.12 A; 424/248.51; 424/250; 424/267; 424/274; 544/142; 544/372; 546/198; 260/326.12 R
[58] Field of Search .............................. 544/142, 372; 260/326.12 R, 326.12 A; 546/198

[56] References Cited

U.S. PATENT DOCUMENTS 3,880,853  4/1975  Demerson et al. ......... 260/326.12 R
3,971,806  7/1976  Brown ........................ 260/326.12 R

*Primary Examiner*—Donald G. Daus
*Assistant Examiner*—James H. Turnipseed
*Attorney, Agent, or Firm*—Wenderoth, Lind & Ponack

[57] ABSTRACT

Tetrahydrothiopyrano[2,3-b]indole derivative represented by the formula I:

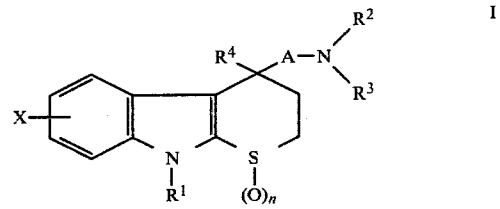

wherein $R^1$ is hydrogen, alkyl, hydroxyalkyl, alkenyl, aralkyl, aryl, —$COR^5$ (wherein $R^5$ is alkyl, alkenyl, aryl or alkoxy) or

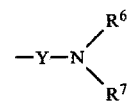

(wherein Y is alkylene, oxoalkylene, hydroxyalkylene and $R^6$ and $R^7$ are each hydrogen or alkyl); $R^2$ is hydrogen or alkyl; $R^3$ is hydrogen, alkyl, hydroxyalkyl, alkenyl, aralkyl, aryl or dialkylaminoalkyl or

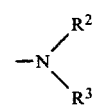

is pyrrolidino, piperidino, piperazino, 4-alkylpiperazino, 4-arylpiperazino or morpholino; $R^4$ is hydrogen or alkyl; A is methylene, alkylmethylene, ethylene, alkylethylene; X is hydrogen or one or two groups selected from the group consisting of halogen, alkyl, alkoxy, hydroxy and halogenoalkyl; and n is an integer of 0 to 2 and its pharmaceutically acceptacle salts; synthesized from 2-propargylthioindole or 2-(4-hydroxy-2-butynylthio)-indole; useful as analgesic and anti-inflammatory agent.

29 Claims, No Drawings

TETRAHYDROTHIOPYRANO[2,3-b]INDOLE DERIVATIVES

The present invention relates to novel tetrahydrothiopyrano[2,3-b]indole derivatives, intermediates, and pharmaceutically acceptable salts thereof and to processes for their preparation.

Antibacterial 4-aminomethyl-9-benzyl-1,2,3,4-tetrahydrocarbazole derivatives are disclosed in U.S. Pat. Nos. 3,939,177 and 3,979,391. However, tetrahydrothiopyrano[2,3-b]indole is a novel condensed ring and it is not known that its derivatives have analgesic and anti-inflammatory activities.

According to this invention there is provided a compound of the formula I:

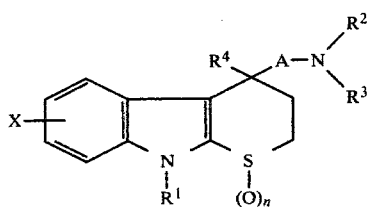

wherein
$R^1$ is hydrogen, alkyl, hydroxyalkyl, alkenyl, aralkyl, aryl, —$COR^5$ (wherein $R^5$ is alkyl, alkenyl, aryl or alkoxy) or

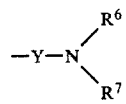

(wherein Y is alkylene, oxoalkylene, hydroxyalkylene and $R^6$ and $R^7$ are each hydrogen or alkyl);
$R^2$ is hydrogen or alkyl;
$R^3$ is hydrogen, alkyl, hydroxyalkyl, alkenyl, aralkyl, aryl or dialkylaminoalkyl or

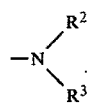

is pyrrolidino, piperidino, piperazino, 4-alkylpiperazino, 4-arylpiperazino or morpholino;
$R^4$ is hydrogen or alkyl;
A is methylene, alkylmethylene, ethylene or alkylethylene;
X is hydrogen or one or two groups selected from the group consisting of halogen, alkyl, alkoxy, hydroxy and halogenoalkyl; and
n is an integer of 0 to 2.
The above compound is called Compound (I) hereinafter.

This invention further provides an intermediate of Compound (I), of the formula:

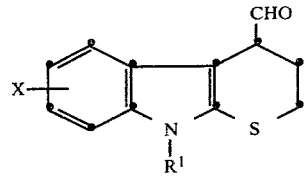

wherein $R^1$ and X are each as defined above.

The following definitions are given for various terms used throughout this specification.

The term "alkyl" refers to both straight- and branched-chain and cyclic aliphatic radicals having from one to six carbon atoms including, e.g. methyl, ethyl, propyl, cyclopropyl, isopropyl, t-butyl, cyclopropylmethyl, pentyl, cyclohexyl and the like. The term "alkenyl" refers to a group having one or more double bonds in the above straight- or branched-alkyl chain, e.g. vinyl, allyl, butenyl, isobutenyl, pentenyl, isopentenyl and the like. "Alkoxy" includes ether radicals having one to six carbon atoms, e.g. methoxy, ethoxy, propoxy, isopropoxy, butoxy, isobutoxy, t-butoxy, pentoxy, methylenedioxy and the like. The term "halogen" refers to chlorine, bromine, and fluorine. "Aryl" includes substituted or non-substituted aromatic ring radicals such as phenyl, naphthyl, furyl, thienyl, oxazolyl, pyridyl, pyrimidyl, benzimidoyl and the like. Substituents on the aromatic ring include those such as alkyl, alkoxy, halogen, hydroxy and the like, preferably being methyl, methoxy and chlorine. The term "hydroxyalkyl", "dialkylaminoalkyl", "halogenoalkyl" and "aralkyl" may be understood from the above description. Namely, these groups include the above alkyl substituted with hydroxy, dialkylamino, halogen or aryl at an optional position. The term "alkylene" refers to both straight- and branched-chain radicals having one to six carbon atoms including, e.g. methylene, ethylene, methylmethylene, trimethylene, ethylmethylene, ethylethylene, propylmethylene, pentamethylene, hexamethylene and the like. The term "oxoalkylene" and "hydroxyalkylene" include the alkylene defined above substituted by oxo or hydroxy at an optional position.

In this invention, the preferable aromatic ring radical is phenyl and the preferable aralkyl is phenylalkyl, more preferably benzyl or phenethyl, especially benzyl.

In the above definition, preferable $R^1$ is hydrogen, alkyl, phenyl or —$COR^5$ wherein $R^5$ is alkyl or phenyl; more preferably, $R^1$ is hydrogen, alkyl, —$COR^5$ wherein $R^5$ is alkyl or phenyl, especially preferable $R^1$ being hydrogen, methyl, isopropyl, acetyl, propionyl and benzoyl, the most preferred being hydrogen. Preferred $R^2$ is hydrogen, or methyl, ethyl or isopropyl and preferred

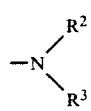

is amino or alkylamino, i.e. preferable is amino, methylamino, ethylamino, isopropylamino, dimethylamino, more preferable being amino and methylamino, especially methylamino. Preferred $R^4$ is hydrogen. Preferred A is methylene and preferable X is hydrogen, methyl, dimethyl, methoxy, dimethoxy, chlorine, fluorine, hydroxy, methylenedioxy, trifluoromethyl, especially hydrogen, dimethyl, the most preferable being hydrogen. Preferred n is 0.

Illustrative of Compound (I) of the invention are:
(1) Compound I of which $R^4$ is hydrogen and n is 0:
4-aminomethyl-2,3,4,9-tetrahydrothiopyrano[2,3-b]indole and the derivatives of which $R^1$ and X are as follows:
 $R^1$ is methyl and X is hydrogen,
 $R^1$ is ethyl and X is hydrogen,
 $R^1$ is isopropyl and X is hydrogen,
 $R^1$ is cyclopropylmethyl and X is hydrogen,
 $R^1$ is hydroxymethyl and X is hydrogen,
 $R^1$ is allyl and X is hydrogen,
 $R^1$ is phenyl and X is hydrogen,
 $R^1$ is benzyl and X is hydrogen,
 $R^1$ is acetyl and X is hydrogen,
 $R^1$ is benzyl and X is hydrogen,
 $R^1$ is acetoxy and X is hydrogen,
 $R^1$ is 2-hydroxy-3-dimethylaminopropyl and X is hydrogen,
 $R^1$ is hydrogen and X is 5,8-dimethyl,
 $R^1$ is hydrogen and X is 6,7-dimethoxy,
 $R^1$ is hydrogen and X is 6-methoxy,
 $R^1$ is hydrogen and X is 8-methoxy,
 $R^1$ is hydrogen and X is 6-methyl,
 $R^1$ is hydrogen and X is 6-hydroxy,
 $R^1$ is methyl and X is 6-hydroxy,
 $R^1$ is hydrogen and X is 6-chloro,
 $R^1$ is hydrogen and X is 6-fluoro, and
 $R^1$ is methyl and X is 6-fluoro,
4-methylaminomethyl-2,3,4,9-tetrahydrothiopyrano[2,3-b]indole and the derivatives of which $R^1$ and X are as follows:
 $R^1$ is methyl and X is hydrogen,
 $R^1$ is ethyl and X is hydrogen,
 $R^1$ is propyl and X is hydrogen,
 $R^1$ is isopropyl and X is hydrogen,
 $R^1$ is isobutyl and X is hydrogen,
 $R^1$ is cyclopropylmethyl and X is hydrogen,
 $R^1$ is phenyl and X is hydrogen,
 $R^1$ is benzyl and X is hydrogen,
 $R^1$ is acetyl and X is hydrogen,
 $R^1$ is propionyl and X is hydrogen,
 $R^1$ is benzoyl and X is hydrogen,
 $R^1$ is p-chlorobenzoyl and X is hydrogen,
 $R^1$ is diethylaminocarbonylmethyl and X is hydrogen,
 $R^1$ is 2-dimethylaminoethyl and X is hydrogen,
 $R^1$ is cyclohexyl and X is hydrogen,
 $R^1$ is butyryl and X is hydrogen,
 $R^1$ is methoxycarbonyl and X is hydrogen
 $R^1$ is phenethyl and X is hydrogen,
 $R^1$ is methylaminomethyl and X is hydrogen,
 $R^1$ is isocrotonoyl and X is hydrogen,
 $R^1$ is hydrogen and X is 8-ethyl,
 $R^1$ is isopropyl and X is 8-ethyl,
 $R^1$ is allyl and X is 8-ethyl,
 $R^1$ is cyclopropylmethyl and X is 8-ethyl,
 $R^1$ is hydrogen and X is 6-hydroxy,
 $R^1$ is methyl and X is 6-hydroxy,
 $R^1$ is acetyl and X is 6-hydroxy,
 $R^1$ is 3-dimethylaminopropyl and X is 7-trifluoromethyl,
 $R^1$ is cinnamoyl and X is 7-trifluoromethyl,
 $R^1$ is 2-hydroxy-3-dimethylaminopropyl and X is 7-trifluoromethyl,
 $R^1$ is 2-hydroxy-3-isopropylaminopropyl and X is 7-trifluoromethyl,
 $R^1$ is isopropyl and X is 7-trifluoromethyl,
 $R^1$ is acetyl and X is 7-trifluoromethyl,
 $R^1$ is propionyl and X is 7-trifluoromethyl,
 $R^1$ is methyl and X is 6-fluoro,
 $R^1$ is ethyl and X is 6-fluoro,
 $R^1$ is isopropyl and X is 6-fluoro,
 $R^1$ is acetyl and X is 6-fluoro,
 $R^1$ is propionyl and X is 6-fluoro,
 $R^1$ is hydrogen and X is 5,8-dimethyl,
 $R^1$ is acetyl and X is 5,8-dimethyl,
 $R^1$ is hydrogen and X is 6,7-methylenedioxy,
 $R^1$ is methyl and X is 6,7-methylenedioxy, and
 $R^1$ is acetyl and X is 6,7-methylenedioxy,
4-ethylaminomethyl-2,3,4,9-tetrahydrothiopyrano[2,3-b]indole and the derivatives of which $R^1$ and X are as follows:
 $R^1$ is methyl and X is hydrogen,
 $R^1$ is isobutyl and X is hydrogen,
 $R^1$ is acetyl and X is hydrogen,
 $R^1$ is benzyl and X is hydrogen,
 $R^1$ is cyclohexyl and X is hydrogen,
 $R^1$ is phenyl and X is hydrogen,
 $R^1$ is hydrogen and X is 5,8-dimethyl and
 $R^1$ is methyl and X is 6-fluoro,
4-propylaminomethyl-2,3,4,9-tetrahydrothiopyrano[2,3-b]indole,
4-isopropylaminomethyl-2,3,4,9-tetrahydrothiopyrano[2,3-b]indole and the derivatives of which $R^1$ and X are as follows:
 $R^1$ is methyl and X is hydrogen
 $R^1$ is acetyl and X is hydrogen,
 $R^1$ is benzoyl and X is hydrogen,
 $R^1$ is hydrogen and X is 5,8-dimethyl,
 $R^1$ is hydrogen and X is 6-fluoro,
 $R^1$ is methyl and X is 6-fluoro, and
 $R^1$ is methyl and X is 6,7-methylenedioxy,
4-butylaminomethyl-2,3,4,9-tetrahydrothiopyrano[2,3-b]indole,
4-t-butylaminomethyl-2,3,4,9-tetrahydrothiopyrano[2,3-b]indole,
4-t-butylaminomethyl-5,8-dimethyl-2,3,4,9-tetrahydrothiopyrano[2,3-b]indole,
4-(2-hydroxyethyl)aminomethyl-2,3,4,9-tetrahydrothiopyrano[2,3-b]indole,
4-allylaminomethyl-2,3,4,9-tetrahydrothiopyrano[2,3-b]indole,
4-dimethylaminomethyl-2,3,4,9-tetrahydrothiopyrano[2,3-b]indole and the derivatives of which $R^1$ and X are as follows:
 $R^1$ is methyl and X is hydrogen,
 $R^1$ is hydroxymethyl and X is hydrogen,
 $R^1$ is acetyl and X is hydrogen,
 $R^1$ is benzoyl and X is hydrogen,
 $R^1$ is phenyl and X is hydrogen, and
 $R^1$ is hydrogen and X is 6-fluoro,
4-(N-isopropyl-N-methylamino)methyl-2,3,4,9-tetrahydrothiopyrano[2,3-b]indole,
4-(N,N-dibutylamino)methyl-2,3,4,9-tetrahydrothiopyrano[2,3-b]indole,
4-cyclopropylaminomethyl-2,3,4,9-tetrahydrothiopyrano[2,3-b]indole, 4-benzylaminomethyl-2,3,4,9-tetrahydrothiopyrano[2,3-b]indole,
4-(p-chlorobenzyl)aminomethyl-2,3,4,9-tetrahydrothiopyrano[2,3-b]indole,
4-(p-methoxybenzyl)aminomethyl-2,3,4,9-tetrahydrothiopyrano[2,3-b]indole,
4-phenethylaminomethyl-2,3,4,9-tetrahydrothiopyrano[2,3-b]indole,
4-phenylaminomethyl-2,3,4,9-tetrahydrothiopyrano[2,3-b]indole,
4-phenylaminomethyl-9-acetyl-2,3,4,9-tetrahydrothiopyrano[2,3-b]indole,
4-(2-N,N-dimethylaminoethyl)aminomethyl-2,3,4,9-tetrahydrothiopyrano[2,3-b]indole,
4-piperidinomethyl-2,3,4,9-tetrahydrothiopyrano[2,3-b]indole,
4-piperazinomethyl-2,3,4,9-tetrahydrothiopyrano[2,3-b]indole,
4-pyrrolidinomethyl-9-methyl-2,3,4,9-tetrahydrothiopyrano[2,3-b]indole,
4-(4-methylpiperazino)methyl-4-methyl-2,3,4,9-tetrahydrothiopyrano[2,3-b]indole,
4-morpholinomethyl-2,3,4,9-tetrahydrothiopyrano[2,3-b]indole,
4-(2-aminoethyl)-2,3,4,9-tetrahydrothiopyrano[2,3-b]indole,
4-(2-N-methylaminoethyl)-2,3,4,9-tetrahydrothiopyrano[2,3-b]indole,
4-(2-N-methylaminoethyl)-9-phenyl-2,3,4,9-tetrahydrothiopyrano[2,3-b]indole, (2) Compound I of which $R^4$ is alkyl and n is 0;
4-methylaminomethyl-4,9-dimethyl-2,3,4,9-tetrahydrothiopyrano[2,3-b]indole, (3) Compound I of which $R^4$ is hydrogen and n is 1 or 2;
4-methylaminomethyl-2,3,4,9-tetrahydrothiopyrano[2,3-b]indole S-oxide,
4-methylaminomethyl-9-acetyl-2,3,4,9-tetrahydrothiopyrano[2,3-b]indole S-oxide,
4-methylaminomethyl-5,8-dimethyl-2,3,4,9-tetrahydrothiopyrano[2,3-b]indole S-oxide,
4-N,N-dimethylaminomethyl-2,3,4,9-tetrahydrothiopyrano[2,3-b]indole S-oxide,
4-methylaminomethyl-2,3,4,9-tetrahydrothiopyrano[2,3-b]indole S-dioxide,
4-methylaminomethyl-9-methyl-2,3,4,9-tetrahydrothiopyrano[2,3-b]indole S-dioxide,
4-methylaminomethyl-6-chloro-2,3,4,9-tetrahydrothiopyrano[2,3-b]indole dioxide, and
4-N,N-dimethylaminomethyl-2,3,4,9-tetrahydrothiopyrano[2,3-b]indole.

The above compounds can be converted to desired pharmaceutically acceptable salts.

Most of the compounds shown above can be prepared from the corresponding 4-formyl derivative as shown below.

Compound (I) of this invention can be prepared by many methods, some of which methods are shown below.

Method I (for preparing 4-aminomethyl derivatives)

Process A (through 4-cyano derivative)

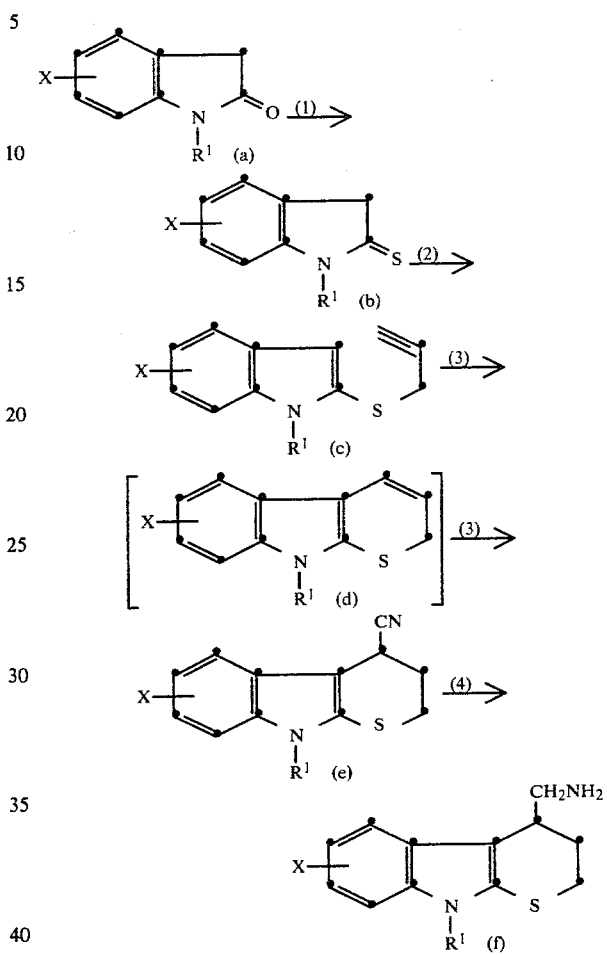

(wherein $R^1$ and X are each as defined above)

This process starts from oxyindole. Substituents $R^1$ can be introduced at any stage of the process. The process is explained by each step following the above schema.

Step (1): The oxo group is substituted with thioxo group at 2 position of oxyindole (a) optionally having substituents at 4, 5, 6, or 7 position by reaction with phosphorus pentasulfide to give Compound (b).

The starting compound 2-oxyindole is easily obtained and many derivatives are known; e.g. 5-chloro-2-oxyindole is described in J. Org. Chem. 33, 4440 (1968); 6-fluoromethyl-2-oxyindole is in ibid. 28, 3580 (1963); 5-methyl-, 5-methoxy- and 5-fluoro-2-oxyindoles are in U.S. Pat. No. 3,882,236; 4,7-dimethyl-2-oxyindole is in Bull. Soc. Chim. 5, 658 (1938); and N-phenyl derivatives are in J. Med. Chem. 15, 762 (1972) and Ber. Deut. Chem. Ges., 47, 2120 (1914). The other starting compounds can be prepared in the same manner as described in these references. Further, 7-ethyl-2-oxyindole can be obtained from 7-ethyl-isatin by usual reducing procedure such as that described in U.S. Pat. No. 3,882,236.

Step (2): Compound (c) can be prepared by reaction of indolin-2-thione (Compound (b)) with propargyl halide in the presence of a base in an inert solvent. Examples of the inert solvent are alcohols (e.g. methanol, ethanol, propanol and the like), benzenes (e.g. benzene, toluene, xylene and the like), ethers (e.g. ether, tetrahydrofuran and the like), acetone, dimethylformamide, pyridine, triethylamine, diethylaniline and the like, which are used solely or combined. Examples of base are potassium carbonate, sodium bicarbonate, potassium bicarbonate, pyridine, sodium methoxide, sodium ethoxide and the like.

Step (3): Compound (c) is heated in an inert solvent, preferably basic solvent to form thiopyran ring followed by reaction with alkali metal cyanide (e.g. potassium cyanide) to give 4-cyano-2,3,4,9-tetrahydrothiopyrano[2,3-b]indole (Compound (e)).

Step (4): The cyano group at 4 position of Compound (e) can be converted to aminomethyl by reduction with metal hydride (e.g. lithium aluminium hydride) or sodium and alcohol, by catalytic reduction or the like.

Process B (through 4-formyl derivative)

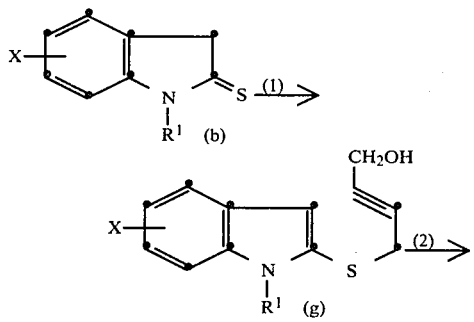

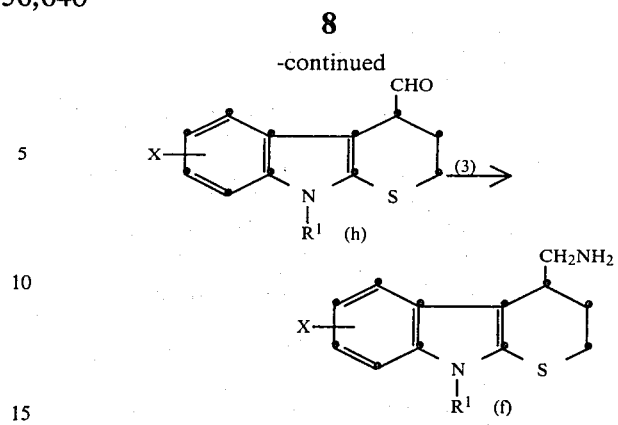

(wherein X and R¹ are each as defined above)

Substituent R¹ can be introduced at any stage in this process.

Step (1): Indolin-2-thione (Compound (b)) is made to react with 4-halogeno-2-butyn-1-ol in the presence of a base to give Compound (g). The base referred to in the above Step (2) of Process A can be used in this step.

Step (2): Compound (g) is heated in an inert solvent, preferably basic solvent to give 4-formyl-2,3,4,9-tetrahydrothiopyrano[2,3-b]indole (Compound (h)). This step is proceeded in the same manner as in the above Step (3) of Process A. The reaction of Compound (h) with hydroxylamine converts the formyl group at 4 position of Compound (h) to hydroxyiminomethyl, which is reduced to aminomethyl with alkali metal hydride (e.g. lithium aluminium hydride).

Method II (for preparing 4-N-monosubstituted aminomethyl derivatives)

Processes A, B and C (starting from 4-aminomethyl derivative)

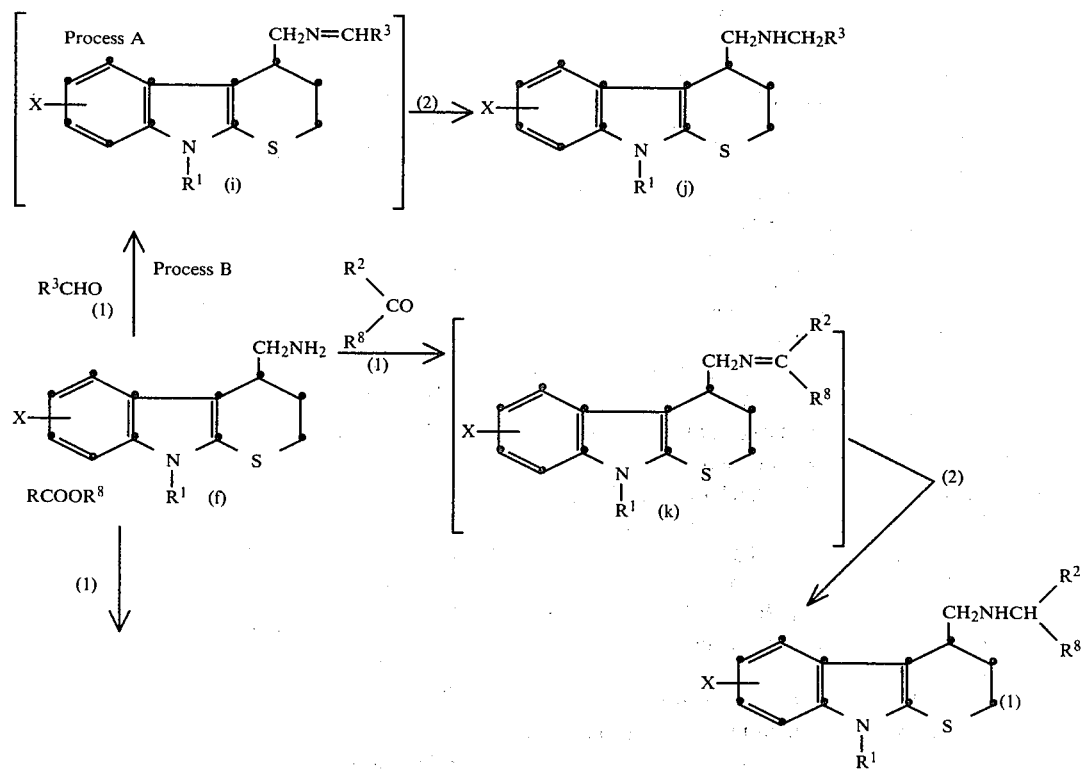

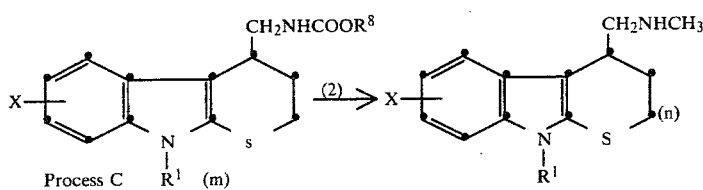

(wherein $R^1, R^2, R^3$ and X are each as defined above, R is halogen, and $R^8$ is alkyl but $R^2$ is not hydrogen)

Process A

Compound (f), 4-aminomethyl-2,3,4,9-tetrahydrothiopyrano[2,3-b]indole and the optionally substituted derivatives are made to react with an aldehyde to form a Schiff base (Step (1)). The Schiff base is reduced to give the objective Compound (j) (Step (2)). The Schiff base can be prepared in an indert solvent or without solvent at room temperature or under heating. The reduction is effected with metal hydride in an inert solvent under heating, if necessary, sodium amalgam and water, sodium and alcohol, or the like. Catalytic reduction can also be employed. As illustrative of metal hydride are lithium aluminium hydride, sodium borohydride, sodium cyanoborohydride and the like. Sodium cyanoborohydride is preferably used since it can be added to the reaction mixture with aldehyde at the same time.

Process B

This process can be effected in the same manner as in Process A except that ketone is used instead of aldehyde.

Process C

This process includes a reaction of Compound (f) alkyl haloformate (Step (1)) and the reaction of the resultant urethane with metal hydride (Step (2)). The condensation with alkyl haloformate may be effected in an inert solvent at room temperature or under heating. The reduction is practised in the same manner as in Process A.

Process D (starting from 4-formayl derivatives)

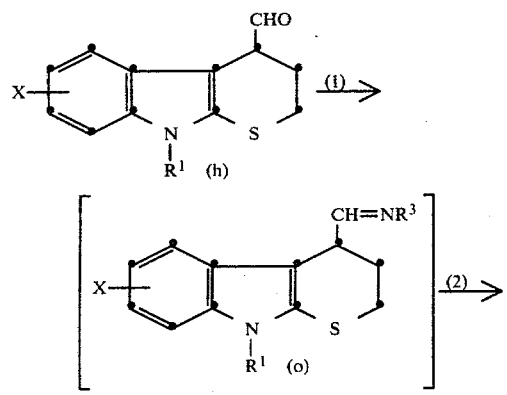

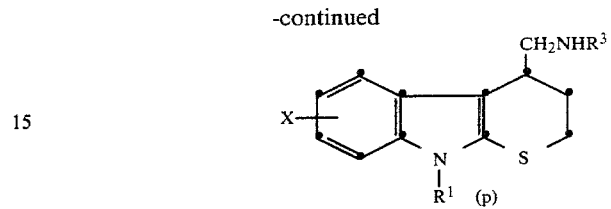

(wherein $R^1$, $R^3$ and X are each as defined above)

Step (1) Compound (h), 4-formyl derivative is made to react with a primary amine to form a Schiff base. The reaction proceeds smoothly at room temperature.

Step (2) This step is the reduction of the Schiff base, i.e. Compound (o) and effected by the same procedure as in the Step (2) of Process A. Generally, the reaction proceeds smoothly at room temperature.

Method III (for preparing 4-N,N-disubstituted aminomethyl derivatives)

Process A (starting from 4-formyl derivative)

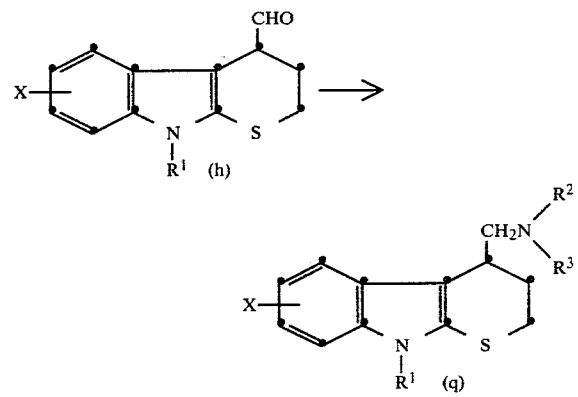

(wherein $R^1$, $R^2$, $R^3$ and X are each as defined above, but $R^2$ and $R^3$ each is not hydrogen)

Compound (q), 4-N,N-disubstituted aminomethyl derivative can be prepared by the reaction of 4-formyl derivative (Compound (h)) with a secondary amine in the presence of a reducing agent. There are exemplified as reducing agent, formic acid, metal hydride, preferably sodium cyanoborohydride, and the like. The reaction may be effected at room temperature or under heating.

Process B (starting from 4-methylamino derivative)

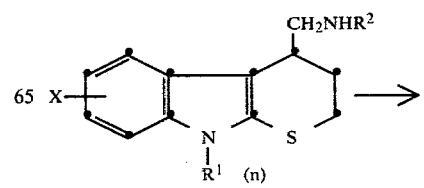

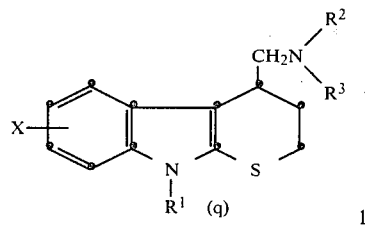

(wherein $R^1$, $R^2$, $R^3$ and X are each as defined above but $R^3$ is not hydrogen).

The starting compound (n) can be prepared by Process A, B, C or D of Method II. In this process, Compound (q) can be prepared by reaction of Compound (n) with an aldehyde in the presence of a reducing agent. Examples of the aldehyde are aliphatic aldehydes (e.g. formaldehyde, acetaldehyde, propionaldehyde, butylaldehyde, and the like) and aromatic aldehydes (e.g. benzaldehyde, phenylacetaldehyde, p-chlorophenylacetaldehyde, p-methoxyacetaldehyde, cinnamaldehyde, 4-formylfuran, 3-formylthiophene and the like). In this process, formic acid or metal hydride described above is preferably used as reducing agent.

The reaction may be effected under cooling or heating or at room temperature. Inert solvent may be used, if necessary.

Method IV (for preparing substituted-2,3,4,9-tetrahydrothiopyrano[2,3-b]indoles)

Substituent can be introduced into 9 position of 2,3,4,9-tetrahydrothiopyrano[2,3-b]indole at any stage of the processes explained in the above methods I, II and III as well as to the final products of these processes. Alternatively, a substituted-2-oxyindole may be used as starting compound to give the desired Compound (I) substituted at 5, 6, 7, 8 and 9 positions. Introduction of substituent into 9 position is effected smoothly if other sensible substituents have been protected with suitable protecting group in a usual manner. It is preferred, for example, to protect a secondary amino group at 4 position with a suitable amino group-protecting group before the introduction. There are exemplified as amino group-protecting group, t-butoxycarbonyl, trifluoroacetyl and the like. Halides are preferably used to introduce substituent into 9 position. Acid anhydrides may be used to introduce acyl group and aldehydes being for hydroxyalkyl group. Introduction of a substituent to 9 position may be effected smoothly if the nitrogen at 9 position is converted to alkali metal salt before the reaction. A substituent at 4 position may be introduced by reaction of a 4-formyl derivative with an alkyl halide.

Method V (for preparing oxides)

Oxide and dioxide of Compound (I) can be prepared by oxidizing an intermediate or a final product of the above processes.

It can be effected with a peracid (e.g. periodic acid, perchloric acid, perbenzoic acid, m-chloroperbenzoic acid and the like) or its salt. The reaction is effected in an inert solvent at room temperature. Method V (modification)

Additionally to the methods described above, any other usual methods used in the organic chemical field can be applied to an intermediate and a final product of the above processes of Method I to IV to obtain a desired Compound (I). For example, formyl group at 4 position of 4-formyl-2,3,4,9-tetrahydrothiopyrano[2,3-b]indole can be converted to 1-alkylaminomethyl by the Grignard reaction followed by oxidation to change the formyl group to acyl and reaction with alkylamine. Aminoalkyl group at 4 position of Compound I can be converted to alkylaminoalkyl with alkyl halide. Method VI Compound (I) of which A is longer than methylene can be prepared by the same reaction as described in Process A of Method I with cyanoacetic acid ester instead of alkali metal cyanide. The process is illustrated as follows:

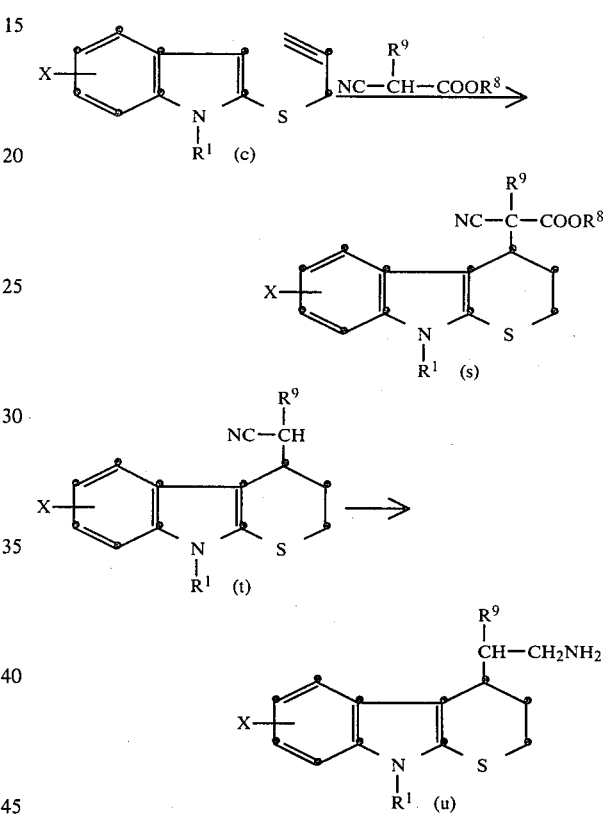

(wherein $R^1$, $R^8$ and X are each as defined above and $R^9$ is is hydrogen or alkyl)

The procedures are all the same as described in Process A of Method I. Compound (u) can be subjected to Processes A, B or C of Method II or Process B of Method III to give the corresponding 4-N-mono-substituted or 4-N,N-disubstituted aminoalkyl derivatives.

The thus-obtained Compound (I) can be converted into its pharmaceutically acceptable non-toxic salts by conventional methods compatible with requirements for such procedure as separation, purification and formulation. The salts include, for example, hydrochloride, hydrobromide, acetate, oxalate, maleate, citrate, tartrate, succinate, sulfate, nitrate, phosphate, thiocyanate, benzoate, salicylate, phthalate and the like, preferably oxalate and hydrochloride.

The compounds of this invention including the pharmaceutically non-toxic salts of Compound (I) exhibit analgesic and anti-inflammatory activities. The pharmacological activity was examined by the following methods, the results being shown in Table 1.

Test Methods

1. Acute Toxicity a. DS male mice (20–25 g) are orally administered a suspension of test compound with gum arabic. The mortality at 72 hours is determined and the $LD_{50}$ is calculated.

b. JCL-Wistar female rats (180–220 g) are orally administered a suspension of test compound with gum arabic. The mortality on the 15th day is determined and the $LD_{50}$ is calculated.

2. Analgesic Activity a. Acetic acid writing method

DS male mice (20–23 g) are treated with an intraperitoneal injection of 0.1 ml/10 g of 0.6% acetic acid 30 minutes after oral administration of a test compound. The number of times of writhing for 10 minutes is counted and $ED_{50}$ is calculated.

b. Foot-licking method

Thirty minutes after oral administration of a test compound in SLC-Wistar female rats (150–170 g), 0.05 ml of 3.7% formaldehyde is subcutaneously injected into the planter tissue of the hind-paw. The number of times of foot-licking syndrome is observed for 50 minutes and the $ED_{50}$ is calculated.

c. Randall and Selitto method

A test compound is orally given SLC-Wistar female rats (150–170 g). Five minutes later 0.1 ml of 20% yeast suspension is subcutaneously injected into the plantar tissue of the foot. The pain threshold is measured by comprissing the foot with a plunger 120 minutes later and the $ED_{50}$ is calculated.

3. Anti-inflammatory Activity

A 0.9% saline solution (0.05 ml) containing 1.0% carrageenin is used as phlogistic agent. After 30 minutes JCL-Wistar female rats (180–200 g) are orally administered a test compound, the phlogistic agent is injected subcutaneously into the plantar of the foots of the rats. The volume of swelling is measured 3 hours later and anti-edema activity is determined by calculating the percentage ratio of the edematous volume of medicated foot of that of non-medicated foot.

TABLE 1

| Test Method Test Compound | Acute Toxicity Mouse $LD_{50}$ mg/kg | Acute Toxicity Rat $LD_{50}$ mg/kg | Analgesic Activity a $ED_{50}$ mg/kg | Analgesic Activity b $ED_{50}$ mg/kg | Analgesic Activity c $ED_{50}$ mg/kg | Anti-inflammatory Activity 50 mg/kg % |
|---|---|---|---|---|---|---|
| Comp. 1 | 409 | 295 | 4.2 | 1.6 | 8.4 | 66 |
| Comp. 2 | 750P | — | 21.2 | 0.54 | 17.8 | 40 |
| Comp. 3 | 750P | — | 11.7 | 2.9 | 19.1 | 25 |
| Comp. 4 | 175P | — | 21 | 4.7 | 15.9 | 44 |
| Mepirizole | 1151 | 552 | 110 | 13 | 130 | — |
| Idomethacin | 17 | 14 | 7 | 65 | 14 | — |

Notes:
P = presumption
— = not done
Comp. 1 = 4-Methylaminomethyl-2,3,4,9-tetrahydrothiopyrano[2,3-b]indole (oxalate)
Comp. 2 = 4-Methylaminomethyl-9-methyl-2,3,4,9-tetrahydrothiopyrano[2,3-b]indole (oxalate)
Comp. 3 = 4-Methylaminoethyl-2,3,4,9-tetrahydrothiopyrano[2,3-b]indole S-dioxide
Comp. 4 = 4-(N,N-dimethyl)aminomethyl-9-acetyl-2,3,4,9-tetrahydrothiopyrano[2,3-b]-indole (hydrochloride)

As shown in Table 1, the above-tested Compounds (I) of this invention exhibit analgesic and anti-inflammatory activities. The analgesic activity is stronger than those of the commercially available compounds, i.e. mepirizole and indomethacin.

Thus, Compound (I) and its pharmaceutically acceptable salts are useful in the treatment of various pains experienced by human beings and other animals.

The compounds of this invention can be administered alone or in combination with pharmaceutically acceptable carriers and other drugs, if necessary, orally, percutaneously or by injection. Preferably, the compounds are used in combination with one or more carriers suited to the particular route of administration. Examples of solid carriers for internal or external use are lactose, sucrose, starch, dextrin, sodium bicarbonate, licorice powder, talc, kaolin, bentonite, calcium carbonate, paraffin and the like, and as gel or liquid carrier, gelatine, water, ethanol, isopropanol, chloroform, glycerol and the like are exemplified.

Practical examples of suitable forms of pharmaceutical preparation of Compound (I) are tablets, capsules, pills, ointments, granules, powders, suppositories, aerosols and injectable solutions.

The invention also provides a therapeutic formulation which comprises 1 mg to 500 mg of one or more Compound (I) with or without a pharmaceutically acceptable carrier. Compound I is generally administered to human adults in amounts of about 3 to about 500 mg per day, though the amount is largely dependent on conditions, e.g. case history, age and sex of patient, adminstration route and the like. The compounds can be adminstered to man either in singlet or divided doses. The compounds may also be administered at once for acute diseases. Thus, the invention includes a method for achieving an analgesic effect in an animal, which method comprises administering to the animal an effective amount of a compound according to this invention.

The invention will now be further illustrated and described by way of examples.

EXAMPLE 1:
4-Aminomethyl-2,3,4,9-tetrahydrothiopyrano-[2,3-b]indole (1) Indolin-2-thione To a suspension of oxyindole (13.3 g) and phosphorous pentasulfide (13.3 g) in tetrahydrofuran (150 ml) is added gradually sodium bicarbonate (16.8 g) at room temperature. After stirring at room temperature for 3 hours, benzene (500 ml) is added thereto. The mixture is washed with water and a saturated saline solution, dried over magnesium sulfate and then evaporated to remove the solvent yielding crude crystals (13.7 g). The product is recrystallized from metanol to give the title compound (11.7 g) melting at 145°–148° C. Yield: 78%

(2) 2-Propargylthioindole

To a solution of the product (14.9 g) of the above (1) in acetone (250 ml) are added potassium carbonate (16.5 g) and propargyl bromide (14.3 g) successively and the mixture is stirred at room temperature for three hours. The precipitate is filtered off. The filtrate is condensed and extracted with ether after addition of water. The extract is washed with water, dried and evaporated to remove the solvent yielding an oily residue (23 g). The residue is chromatographed on a column of silica gel (100 g) and eluted with benzene-hexane. The eluate is condensed to give the tile compound as an oil (18.3 g). Yield: 98%

IR: $\nu_{max}^{CCl_3}$ 3450, 3300 cm$^{-1}$

Anal. Calcd. for $C_{11}H_9NS$: C, 70.55; H, 4.84; N, 7.48; S, 17.12. Found: C, 70.28; H, 4.89; N, 7.66; S, 17.00.

(3) 4-Cyano-2,3,4,9-tetrahydrothiopyrano[2,3-b]indole

The product of the above (2) (13.2 g) is dissolved in a mixture of ethanol (300 ml) and triethylamine (20 ml). The solution is refluxed for 1 hour and further 2 hours after addition of a solution of potassium cyanate (25 g) in a mixture of ethanol (170 ml) and water (80 ml) and evaporated to remove the solvent. The residue is extracted with ether after addition of water. The extract is washed with water, dried and evaporated to remove the solvent. The oily residue (15 g) is chromatographed on an column of silica gel (450 g) and eluted with benzene. The eluate is condensed to give the title compound as crystals melting at 125°-126° C. Yield: 69%

IR: $\nu_{max}^{CHCl_3}$ 3440, 2230 cm$^{-1}$

Anal. Calcd. for $C_{12}H_{10}N_2S$: C, 67.26; H, 4.70; N, 13.07; S, 14.96. Found: C, 66.97; H, 4.61; N, 12.82; S, 15.07.

(4) 4-Aminomethyl-2,3,4,9-tetrahydrothiopyrano[2,3-b]indole

To a solution of aluminum chloride (18.7 g) and lithium aluminium hydride (5.5 g) in absolute ether (200 ml) is added dropwise a solution of the product of the above (3) (12 g) in absolute ether (300 ml) at room temperature. The solution is stirred at room temperature for 45 minutes and a 20% aqueous solution (65 ml) of sodium hydroxide is added dropwise under ice-cooling. The precipitate is filtered off. The ether layer of the filtrate is separated, washed with water, dried and evaporated to give an oil (5.1 g). The precipitate mentioned above is suspended in water, made alkaline with a 20% aqueous solution of sodium hydroxide, and extracted with ether. The extract is washed with water, dried and evaporated to give an oil (5.3 g). Both the oil are combined and treated with oxalic acid in ether to give the oxalate (15 g) of the title compound melting at 238° C. (decomp.).

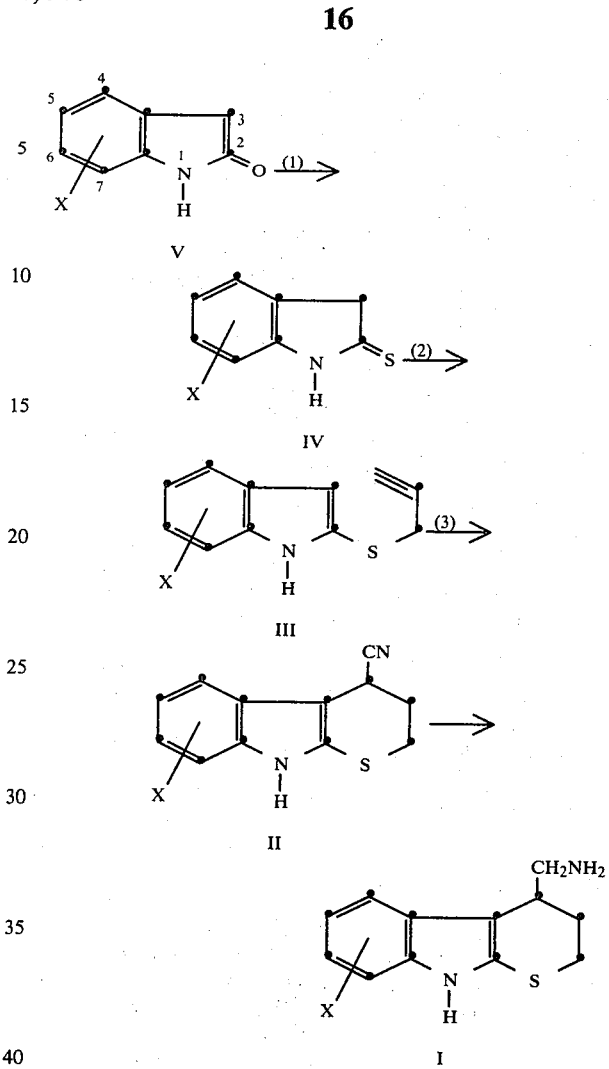

The product is suspended in water, made alkaline with a 20% aqueous solution of sodium hydroxide and extracted with ether. The extract is condensed to give an oil (9.4 g), which is crystallized from ethanol-hexane-ether to give crystals (8.8 g) of the title compound melting at 122°-125° C. Yield: 72%

IR: $\nu_{max}^{CHCl_3}$ 3450 cm$^{-1}$ (free base)

Anal. Calcd. for $C_{12}H_{14}N_2S$: C, 66.02; H, 6.46; N, 12.28; S, 14.69. Found: C, 66.24; H, 6.51; N, 12.72; S, 14.51.

EXAMPLES 2-4

The compounds in Table 2 can be prepared by the same procedure as in Example 1 as shown in the schema.

TABLE 2

| Ex. No. | V X | IV mp(°C.) | III mp(°C.) | III Yield (%) | II mp(°C.) | II Yield (%) | I mp(°C.) | I Yield (%) |
|---|---|---|---|---|---|---|---|---|
| 2 | 5-Cl | 165-175 | oil | 90 | 190-192 | 52 | 156-158 | 70 |
| 3 | 5-CH$_3$O | 179-182 | 44-46 | 96 | 148-150 | 54 | 164-166 | 63 |
| 4 | 5-CH$_3$ | 158-162 | oil | 90 | oil | 53 | 125-127 | 46 |

EXAMPLE 5:
4-Benzylaminomethyl-2,3,4,5-tetrahydrothiopyrano[2,3-b]indole (1) To a solution of the product of Example 1 (595 mg) in ethanol (8 ml) is added a solution of benzaldehyde (304 mg) in ethanol (4 ml) under cooling. The mixture is stirred at room temperature for 1.5 hours and then evaporated to remove the solvent. The residue is dissolved in tetrahydrofuran (20 ml) and added dropwise to a suspension of lithium aluminium hydride (359 mg) in tetrahydrofuran (40 ml). The mixture is refluxed for 2 hours and water and a 10% aqueous solution of sodium hydroxide are added thereto under ice-cooling. The precipitate is filtered off. The filtrate is washed with a saline solution, dried and evaporated to give an oil. The oil is crystallized from ethyl acetate-petroleum benzine to give the title compound (741 mg) as colorless needles melting at 117.5°–118° C. Yield: 88%

IR: $\nu_{max}^{CHCl_3}$ 3450 cm$^{-1}$

NMR: $\delta_{CDCl_3}$ 2.0–3.5m5H, 3.81s2H, 7.27s5H, 6.9–7.5m, 7.85brs

Anal. Calcd. for $C_{19}H_{20}N_2S$: C, 73.99; H, 6.54; N, 9.08. Found: C, 73.97; H, 6.61; N, 9.33.

(1a) To a solution of 4-aminomethyl-2,3,4,9-tetrahydrothiopyrano[2,3-b]indole (150 mg) in methanol (5 ml) are added a solution of benzaldehyde (76 mg) in methanol (1.5 ml) and sodium cyanoborohydride (132 mg). The mixture is adjusted to pH 7 with a solution of hydrochloride in methanol, stirred at room temperature for 1 hour and evaporated to remove the solvent. The residue is dissolved in ether, washed with a 10% aqueous solution of sodium hydroxide and a saline solution, dried and evaporated to give the title compound (210 mg).

EXAMPLES 6-7

The following compounds can be prepared by the same procedure as in Example 5(1).

(1) 4-(p-Chlorobenzylaminomethyl)-2,3,4,9-tetrahydrothiopyrano[2,3-b]indole, mp. 155°–156.5° C. Yield: 93%

IR: $\nu_{max}^{Nujol}$ 3270 cm$^{-1}$

Anal. Calcd. for $C_{19}H_{19}N_2SCl$: C, 66.55; H, 5.59; N, 8.17. Found: C, 66.53; H, 5.60; N, 8.34.

(2) 4-(p-Methoxybenzylaminomethyl)-2,3,4,9-tetrahydrothiopyrano[2,3-b]indole mp. 133°–134° C. Yield: 81%

IR: $\nu_{max}^{CHCl_3}$ 3460 cm$^{-1}$

NMR: $\delta_{CDCl_3}$ 3.68s3H, 3.87s2H

Anal. Calcd. for $C_{20}H_{22}N_2OS$: C, 70.97; H, 6.55; N, 8.27. Found: C, 70.94; H, 6.64; N, 8.20.

EXAMPLE 8:
4-Isopropylaminomethyl-2,3,4,9-tetrahydrothiopyrano[2,3-b]indole A solution of 4-aminomethyl-2,3,4,9-tetrahydrothiopyrano[2,3-b]indole (1.0 g) in acetone (10 ml) is kept at room temperature for 30 minutes and then heated at 50° C. for 5 minutes. The solution is cooled with ice. The colorless precipitate is collected by filtration to give 4-isopropylideneaminomethyl-2,3,4,9-tetrahydrothiopyrano[2,3-b]indole (1.07 g) melting at 173° C. (decomp.).

Anal. Calcd. for $C_{15}H_{18}N_2S$: C, 69.73; H, 7.02; N, 10.84. Found: C, 69.83; H, 7.04; N, 10.67.

The product (1.07 g) is treated with lithium aluminium hydride in the same manner as in Example 5(1) to give crude crystals (1.29 g). Recrystallization from ethyl acetate-petroleum benzine gives colorless crystals (985 mg) of the title compound melting at 106°–108° C. Yield: 91%

IR: $\nu_{max}^{CHCl_3}$ 3470 cm$^{-1}$

Anal. Calcd. for $C_{15}H_{20}N_2S$: C, 69.19; H, 7.47; N, 10.78 Found: C, 69.05; H, 7.72; N, 10.78

EXAMPLE 9:
4-Methylaminomethyl-2,3,4,9-tetrahydrothiopyrano[2,3-b]indole

To a solution of 4-aminomethyl-2,3,4,9-tetrahydrothiopyrano[2,3-b]indole (2.72 g) in a mixture of tetrahydrofuran (55 ml) and triethylamine (3.4 ml) is added dropwise a solution of ethyl chlorocarbonate (1.41 g) in tetrahydrofuran (20 ml). The solution is stirred at room temperature for 5 hours, diluted with ether and washed with 3 N hydrochloric acid, water, an aqueous solution of sodium bicarbonate and water successively. Then, the solution is dried and evaporated to give an oil (3.47 g). The oil is chromatographed on a column of silica gel (140 g) and eluted with benzene-hexane (4:1). The eluate is evaporated to give 4-(N-ethoxycarbonylaminomethyl)-2,3,4,9-tetrahydrothiopyrano[2,3-b]indole (3.50 g).

IR: $\nu_{max}^{CHCl_3}$ 3640, 1710 cm$^{-1}$

The product (3.5 g) is treated with lithium aluminium hydride in the same manner as in Example 5(1) to give an oil. The oil is treated with oxalic acid in ethanol to give the oxalate (3.4 g) of the title compound melting at 239° C. (decomp.). Yield: 85%

Anal. Calcd. for $C_{15}H_{18}N_2O_4S$: C, 55.88; H, 5.62; N, 8.69. Found: C, 55.82; H, 5.61; N, 8.42.

EXAMPLE 10:
4-Dimethylaminomethyl-2,3,4,9-tetrahydrothiopyrano[2,3-b]indole To a solution of 4-aminomethyl-2,3,4,9-tetrahydrothiopyrano[2,3-b]indole (1.8 g) in tetrahydrofuran (80 ml) are added acetic acid (2.3 ml), 37% formalin (5.6 ml) and sodium cyanoborohydride (1.35 g) successively. The mixture is stirred at room temperature for 1 hour and evaporated to remove the solvent. The residue is extracted with ether after addition of some pieces of ice and an 10% aqueous solution of sodium hydroxide. The extract is washed with water, dried and evaporated to give an oil (3 g). The oil is chromatographed on a column of basic alumina (70 g) and eluted with ethyl acetate-hexane (1:1). The eluate is evaporated to give crystals of the title compound (1.34 g) melting at 121°–122° C. Yield: 66%

Anal. Calcd. for $C_{14}H_{18}N_2S$: C, 68.25; H, 7.36; N, 11.37. Found: C, 68.14; H, 7.30; N, 11.32.

EXAMPLE 11:
4-Dibutylaminomethyl-2,3,4,9-tetrahydrothiopyrano[2,3-b]indole The title compound can be prepared by the same procedure as in Example 10 using propionaldehyde instead of formalin. Yield: 80%. Mp. 175°–178° C. (oxalate).

EXAMPLE 12:
4-Methylaminomethyl-2,3,4,9-tetrahydrothiopyrano[2,3-b]indole (1) 2-(4-hydroxy-2-butynylthio)indole To a solution of 2-indolinthione (7.45 g) in acetone (75 ml) is added potassium carbonate (7.60 g). After stirring, 4-chloro-2-butyn-1-ol (5.48 g) is added thereto. The mixture is stirred at room temperature for 5 hours and filtered. The filtrate is condensed to remove the acetone completely. The residue is dissolved into diethylamine (10 ml), kept at room temperature for 1 hour and evaporated to remove the diethylamine aiming to remove excessive agents. The residue is dissolved in ether (250 ml), washed with water, 2 N hydrochloric acid, water and a saturated saline solution successively, dried and evaporated to give the title compound as an oil (12.0 g).

IR: $\nu_{max}^{CHCl_3}$ 3600, 3450 cm$^{-1}$

NMR: $\delta_{CDCl_3}$ 2.01s1H, 3.57t(2)2H, 4.27t(2)2H, 6.80t(2)1H (2) 4-Formyl-2,3,4,9-tetrahydrothiopyrano[2,3-b]indole A solution of the product of the above (1) (12.0 g) in pyridine (120 ml) is heated at 100° C. for 2 hours and evaporated to remove the pyridine. The residue is dissolved in ether (300 ml), washed with water, 2 N hydrochloric acid and a saturated saline solution, dried and evaporated to remove the solvent. The residue (11.0 g) is chromatographed on silica gel (50 g) and eluted with benzene. The eluate is evaporated to give the title compound as an oil (8.14 g). The oil is gradually solidified in a refrigerator.

Mp. 60°–65° C.

IR: $\nu_{max}^{CHCl_3}$ 3450, 1720 cm$^{-1}$

Anal. Calcd. for $C_{12}H_{11}NOS$: C, 66.33; H, 5.10; N, 6.45; S, 14.76. Found: C, 66.16; H, 5.15; N, 6.20; S, 14.64.

(3) 4-Methylaminomethyl-2,3,4,9-tetrahydrothiopyrano[2,3-b]indole

To a solution of the product of the above (2) (2.17 g) in absolute methanol (10 ml) is added a 30% solution (2.2 ml) of methylamine in methanol. The mixture is stirred at room temperature for 1 hour. Sodium borohydride (380 mg) is added to the filtrate. The mixture is stirred at room temperature for 2 hours and evaporated to remove the solvent. The residue is acidified with 2 N hydrochloric acid after addition of water. The solution is extracted with chloroform to remove neutral impurities. The aqueous layer is made alkaline with an aqueous solution of sodium hydroxide and extracted again with chloroform. The extract is washed with water, dried and evaporated to remove the solvent. The residue is treated with small amount of benzene to give the 1/6 benzene adduct (2.21 g) of the title compound melting at 78°–81° C. Yield: 90%

IR: $\nu_{max}^{CHCl_3}$ 3460, 3300 cm$^{-1}$

NMR: $\delta_{CDCl_3}$ 2.48s3H, 7.40s1H

Anal. Calcd. for $C_{13}H_{16}N_2S.1/6\ C_6H_6$: C, 68.53; H, 6.98; N, 11.42; S, 13.07. Found: C, 68.36; H, 6.97; N, 11.38; S, 13.03.

Mp. 245°–250° C. (decomp.) (hydrochloride)

Anal. Calcd. for $C_{13}H_{17}N_2SCl$: C, 58.09; H, 6.37; N, 10.42; S, 11.93. Found: C, 58.27; H, 6.39; N. 10.50; S, 11.90.

Mp. 246°–248° C. (decomp.) (methylsulfonate)

Anal. Calcd. for $C_{14}H_{20}N_2O_3S$: C, 51.20; H, 6.14, N, 8.53; S, 19.52. Found: C, 51.42; H, 6.11; N, 8.43; S, 19.27.

EXAMPLES 13–29

Compound I in Table 4 is obtained by the same procedure as in Example 12(1)-(3) using Compound IV prepared by the same procedure as in Example 1(1) as illustrated in the following schema. Physical constants of starting Compounds II, III, IV and V are shown in Table 3.

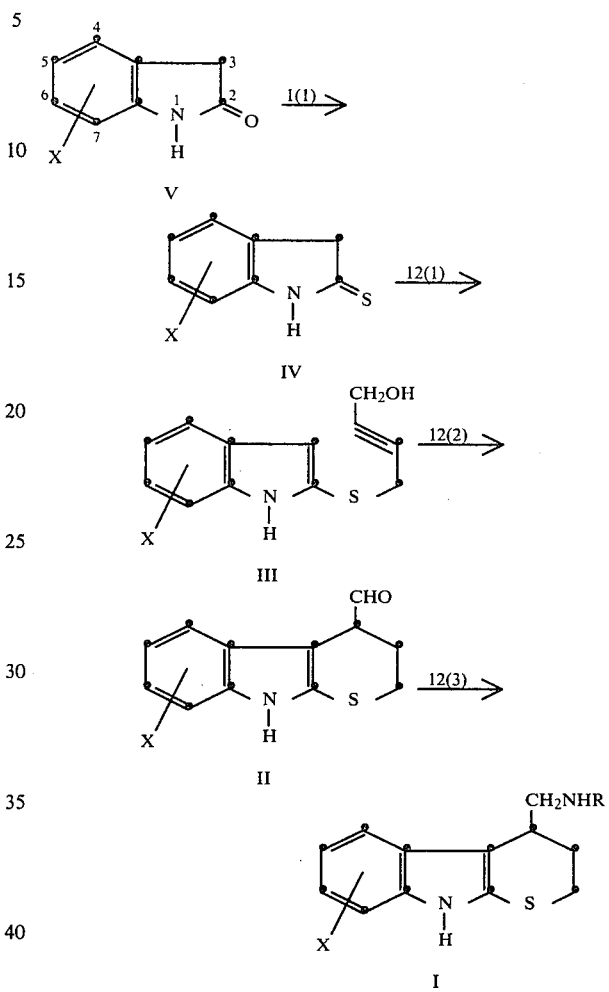

TABLE 3

| | Compound | | | | |
|---|---|---|---|---|---|
| | IV | | III | II | |
| V X | mp(°C.) | Yield (%) | mp (°C.) | mp(°C.) | Yield (%) |
| 4,7-diMe | 208.5–212(d) | 69.3 | oil | 190.5–192(d) | 81.2 |
| 7-Et | 163–166 | 65.4 | " | 154–157 | 74 |
| 6-CF$_3$ | 180–183 | 72.5 | " | 139–141 | 75.1 |
| 5-F | 167–173 | 78.7 | " | 94.5–96 | 76.3 |

TABLE 4

| Ex. No. | X | R | Salt or Adduct | mp. (°C.) | Elemental Analysis Calcd: Found: | | | | NMR:$\delta^{CDCl_3}$ (Free Base) | Yield (II)→I) % |
|---|---|---|---|---|---|---|---|---|---|---|
| | | | | | C | H | N | S | | |
| 13 | H | Et | HBr | 209–211(d) | $C_{14}H_{19}N_2SBr$ 51.38 51.42 $C_{15}H_{21}N_2SCl$ | 5.85 5.95 | 8.56 8.30 | 9.80 9.66 | 1.10t(7)3H, 2.75q(7)3H. | 64 |

TABLE 4-continued

| Ex. No. | X | R | Salt or Adduct | mp. (°C.) | Elemental Analysis Calcd: Found: C H N S | NMR:δ$^{CDCl_3}$ (Free Base) | Yield (II)→I) % |
|---|---|---|---|---|---|---|---|
| 14 | H | Pr | HCl | 245–250(d) | 60.69– 7.13 9.44 10.80<br>60.93 7.18 9.35 10.93<br>$C_{20}H_{26}N_2O_4S$ | — | 70 |
| 15 | H | ⟨H⟩– | (COOH)₂ | 230–232(d) | 61.52 6.71 7.17 8.21<br>61.59 6.65 7.12 8.04<br>$C_{20}H_{20}N_2O_4S$ | — | 75 |
| 16 | H | Ph– | (COOH)₂ | 173–175(d) | 62.48 5.24 7.29 8.34<br>62.43 5.27 7.01 8.50<br>$C_{16}H_{22}N_2O_3S_2$ | — | 20 |
| 17 | H | CH₂=CHCH₂– | CH₃SO₃H | 245–248(d) | 54.21 6.26 7.90 18.09<br>54.44 6.33 7.71 17.79<br>$C_{20}H_{22}N_2S$ | 5.23m(2H),<br>5.97m(1H) | 72 |
| 18 | H | PhCH₂CH₂– | — | 110–111 | 74.49 6.88 8.69 9.94<br>74.35 6.94 8.45 10.10<br>$C_{19}H_{33}N_3O_2SBr_2$ | 6.9–7.5m(9H). | 80 |
| 19 | H | (CH₃)₂NHCH₂CH₂– | 2HBr . CH₃COOC₂H₅ | 127–129(d) | 43.27 6.31 7.97 6.08<br>43.14 6.06 7.99 5.94<br>$C_{14}H_{18}N_2OS$ . 1/6H₂O | 2.20s(6H) | 85 |
| 20 | H | HOCH₂CH₂– | 1/6H₂O | 138–139 | 63.36 6.96 10.56 12.08<br>63.27 6.90 10.43 12.25<br>$C_{16}H_{23}N_2ClS$ | 2.73t(6)2H;<br>3.63t(6)2H.<br>(in CD₃OD) | 69 |
| 21 | 5,8-diMe | Me | HCl | 277.5–280 | 60.69 7.13 9.44<br>60.69 7.27 9.38<br>$C_{16}H_{23}N_2ClS$ | 2.35s3H,<br>2.65s3H,<br>2.42s | 85 |
| 22 | 5,8-diMe | Et | HCl | 270–275 | 61.82 7.46 9.01<br>61.61 7.60 9.26<br>$C_{17}H_{25}N_2ClS$ | 2.35s3H,<br>2.63s3H,<br>1.10t(7) | 76 |
| 23 | 5,8-di-Me | i-Pr | HCl | 281–285 | 62.84 7.76 8.62<br>62.76 7.65 8.42<br>$C_{20}H_{28}N_2O_4S$ | 2.33s3H,<br>2.63s3H,<br>1.03d(6),<br>1.05d(6) | 83 |
| 24 | 5,8-diMe | t-Bu | (COOH)₂ | 289–293 | 61.20 7.19 7.14<br>61.07 7.12 7.07<br>$C_{17}H_{22}N_2O_4S$ | 2.35s3H,<br>2.64s3H,<br>1.10s9H. | 65 |
| 25 | 8-Et | Me | (COOH)₂ | 225–229(d) | 58.27 6.33 7.99<br>58.06 6.22 7.83<br>$C_{14}H_{16}ClF_3N_2S$ | 1.30t(7)3H,<br>3.33d(1)<br>7.75d-q(6,1)<br>8.28brs. | 78 |
| 26 | 7-CF₃ | Me | HCl | 183–187(d) | 49.93 4.79 8.32<br>49.88 5.03 8.10<br>$C_{15}H_{17}FN_2O_4S$ | 2.47s3H,<br>IR:ν$_{max}^{CHCl_3}$<br>3470 cm⁻¹ | 79 |
| 27 | 6-F | Me | (COOH)₂ | 217–223(d) | 52.93 5.03 8.23<br>52.92 5.26 7.93<br>$C_{16}H_{19}FN_2O_4S$ | 2.45s3H,<br>8.95brs | 74 |
| 28 | 6-F | Et | (COOH)₂ | 203–205(d) | 54.23 5.40 7.90<br>54.03 5.58 7.71<br>$C_{15}H_{20}ClFN_2S$ | 1.10t(7)3H | 61 |
| 29 | 6-F | i-Pr | HCl | >280 | 57.22 6.40 8.90<br>57.08 6.58 8.79 | 1.05d(6)3H,<br>1.06d(6)3H, | 81 |

(Notes)
Each abbreviation has the following meaning through this specification.
Me = methyl,
Et = ethyl,
Pr = propyl,
Bu = butyl,
Ph = phenyl.

EXAMPLE 30:
4-Dimethylaminomethyl-2,3,4,9-tetrahydrothiopyrano[2,3-b]indole

To a 20% solution (5.8 ml) of dimethylamine in methanol is added 98% formic acid (940 mg). The solution is heated to remove the methanol. A solution of 4-formyl-2,3,4,9-tetrahydrothiopyrano[2,3-b]indole (2.17 g) in benzene (10 ml) is added dropwise thereto at 70°–80° C.

The mixture is refluxed for 5 hours and evaporated to remove the solvent. The residue is made alkaline with an aqueous solution of sodium hydroxide and extracted with chloroform. The extract is washed with water, dried and evaporated to remove the solvent. The residue is crystallized from methanol to give the title compound (1.74 g) melting at 122°–124° C. Yield: 71%

IR: $\nu_{max}^{CHCl_3}$ 3460 cm$^{-1}$ (free base)

Anal. Calcd. for $C_{14}H_{18}N_2S$: C, 68.25; H, 7.36; N, 11.37; S, 13.01. Found: C, 68.30; H, 7.43; N, 11.29; S, 13.12.

EXAMPLES 31–34:

The compounds in Table 5 are prepared by the same procedure as in Example 30.

Anal. Calcd. for $C_{14}H_{11}NS$: C, 74.63; H, 4.92; N, 6.22; S, 14.23. Found: C, 74.61; H, 4.99; N, 6.06; S, 14.42.

(2) 1-Phenyl-2-(4-hydroxy-2-butenylthio)indole

To a solution of the product of the above (1)(2.2 g) in acetone (20 ml) are added potassium carbonate (1.54 g) and 4-chloro-2-butyn-1-ol (1.03 g). The mixture is stirred for 4 hours and filtered. The filtrate is condensed at below the room temperature. The oily residue is dissolved in benzene and evaporated at below the room temperature. Ether is added to the residue and then a 30% solution (1.5 ml) in methylamine in methanol on ice bath. The mixture is stirred for 30 minutes and after addition of ether, washed with ice-cooled 3 N-hydrochloric acid, water, an aqueous solution of sodium bi-

TABLE 5

| Ex. No. | N(R²)(R³) | Salt or Adduct | mp. (°C.) | Elemental Analysis Calcd.: Found: C | H | N | S | Yield % |
|---|---|---|---|---|---|---|---|---|
| 31 | N-piperidinyl | (COOH)₂ | 226–228(d) | $C_{19}H_{24}N_2O_4S$ 60.62 60.54 | 6.43 6.34 | 7.44 7.26 | 8.25 8.59 | 84 |
| 32 | N(piperazinyl-N-Me) | H₂O | 153–155 | $C_{17}H_{27}N_3O_2S$ 63.91 63.71 | 7.89 8.14 | 13.15 13.44 | 10.04 9.77 | 60 |
| 33 | N(Bu)(Bu) | (COOH)₂ | 175–178 | $C_{22}H_{32}N_2O_4S$ 62.83 62.51 | 7.67 7.72 | 6.66 6.46 | 7.62 7.67 | 83 |
| 34 | N(piperazinyl-N-Ph) | HCl | 248–255 | $C_{22}H_{26}N_3SCl$ 66.06 65.87 | 6.55 6.72 | 10.05 10.55 | 8.02 8.20 | 49 |

EXAMPLE 35:
4-Aminomethyl-9-phenyl-2,3,4,9-tetrahydrothiopyrano[2,3-b]indole (1) 1-Phenylindoline-2-thione To a solution of N-phenyloxyindole (1 g) in tetrahydrofuran (20 ml) are added phosphorus pentasulfide (2.6 g) and sodium bicarbonate (1 g). The mixture is stirred overnight and evaporated to remove the solvent. The residue is dissolved in water with vigorous stirring. The solution is adjusted to pH 8–9 with an aqueous solution of sodium bicarbonate and extracted with benzene. The extract is washed with water, dried and evaporated to give the title compound as yellow powder (800 mg) melting a 104°–106° C. Recrystallization from ether-petroleum benzine gives yellow crystals melting at 106°–107° C.

NMR: $\delta_{CDCl_3}$ 4.25s2H, 6.6–7.7m9H.

carbonate and water successively. The ether layer is dried and evaporated to give the title compound as an oil (3.1 g). The oil is chromatographed on a column of silica gel and eluted with hexane-benzene (1:10) benzene and ether-benzene (1:100) successively. The title compound is obtained as colorless oil.

IR: $\nu_{max}^{CHCl_3}$ 3600 cm$^{-1}$.

NMR: $\delta_{CDCl_3}$ 1.64brs1H, 3.27t(2)2H, 4.09brs(w½=13), 6.87s1H, 7.44s5H.

(3) 4-Aminomethyl-9-phenyl-2,3,4,9-tetrahydrothiopyrano[2,3-b]indole.L-tartrate

A solution of the product of the above (2) (3.71 g) in pyridine (75 ml) is heated at 110° C. for 70 minutes. After cooling, methanol (25 ml) and hydroxyamine hydrochloride (2.2 g) are added thereto. The mixture is stirred at room temperature for 50 minutes and evaporated. The residue is acidified with ice-cooled 3 N- hydrochloric acid and extracted with chloroform. The extract is evaporated to give oily residue. The residue is chromatographed on a column of silica gel and eluted with benzene. The eluate is evaporated to give 4-hydroxyiminomethyl-9-phenyl-2,3,4,9-tetrahydrothiopyrano[2,3-b]indole (3.28 g). The product is dissolved into tetrahydrofuran (55 ml) and lithium aluminium hydride (1.4 g) is added thereto at room temperature. The mixture is refluxed for 1 hour. Ethyl acetate, an 10% aqueous solution of sodium hydroxide and water are successively added thereto. The precipitate is collected by filtration, washed with ethyl acetate and chloroform, and added to the filtrate. The organic layer is separated, washed with water, dried and evaporated to give the free base of the title compound as an oil.

The oil (3 g) is dissolved in ethyl acetate. A solution of L-tartaric acid in ethyl acetate-methanol is added thereto to give the tartrate of the title compound (3.0 g) melting at 196°–198° C. (decomp.).

Anal. Calcd. for $C_{22}H_{24}N_2O_6S$: C, 59.45; H, 5.44; N, 6.30; S, 7.21. Found: C, 59.37; H, 5.72; N, 6.28; S, 7.03.

EXAMPLE 36:
4-Dimethylaminomethyl-9-phenyl-2,3,4,9-tetrahydrothioyrano[2,3-b]indole (1)

4-Formyl-9-phenyl-2,3,4,9-tetrahydrothiopyrano[2,3-b]indole

The product of the above Example 35(2) (200 mg) is dissolved in a mixture of toluene (2 ml) and pyridine (0.1 ml) and refluxed for 30 minutes. Evaporation of the solvents gives the title compound (190 mg).

IR: $\nu_{max}^{CHCl}$ 1720 cm$^{-1}$

NMR: $\delta_{CDCl_3}$ 7.49 s5H, 9.84d(2)1H (2)

4-Dimethylaminomethyl-9-phenyl-2,3,4,9-tetrahydrothiopyrano[2,3-b]indole

Dimethylamine hydrochloride (1.74 g) is dissolved in absolute methanol (18 ml) and sodium methoxide (813 mg) is added thereto. To the solution are added a solution of the product of the above (1), (1.1 g) in tetrahydrofuran (10 ml) and sodium cyanoborohydride (1 g). The mixture is stirred at room temperature overnight and evaporated after addition of an aqueous solution (4 ml) of sodium hydroxide. The residue is extracted with ether after addition of water and a 10% aqueous solution of sodium hydroxide. The extract is condensed to give the title compound as an oil (1.10 g). The oil is treated with L-tartaric acid (443 mg) in ethanol to give the tartrate (750 mg) melting at 172°–177° C. (decomp.).

NMR: $\delta_{CDCl_3}$ 2.37s6H, 7.48s5H (free base)

Anal. Calcd. for $C_{24}H_{28}N_2O_6S$: C, 61.00; H, 5.97; N, 5.93; S, 6.79. Found: C, 61.00; H, 5.74; N, 6.00; S, 6.80.

The same procedure gives the oxalate melting at 230° C. (decomp.).

Anal. Calcd. for $C_{22}H_{24}N_2O_4S$: C, 64.06; H, 5.86; N, 6.79; S, 7.77. Found: C, 64.10; H, 6.03; N, 6.59; S, 7.71.

EXAMPLE 37:
4-Methylaminomethyl-9-phenyl-2,3,4,9-tetrahydrothiopyrano[2,3-b]indole To a solution of 4-formyl-9-phenyl-2,3,4,9-tetrahydrothiopyrano[2,3-b]indole (1.4 g) in absolute benzene (20 ml) is added a 30% solution (1.5 ml) of methylamine in methanol. The mixture is stirred at room temperature for 3 hours and evaporated to give 4-methyliminomethyl-9-phenyl-2,3,4,9-tetrahydrothiopyrano[2,3-b]indole as orange solid. The product is dissolved in a mixture of methanol (20 ml) and tetrahydrofuran (20 ml) and sodium borohydride (274 mg) is added thereto. The mixture is stirred at room temperature for 1 hour and evaporated.

The residue is extracted with ether after addition of water and a 10% aqueous solution of sodium hydroxide. The extract is condensed to give the title compound as an oil (1.3 g). The product is treated with hydrochloric acid in ethanol to give the hydrochloride (1.25 g) melting at 253° C. (decomp.).

Anal. Calcd. for $C_{19}H_{21}N_2SCl$: C, 66.17; H, 6.14; N, 8.12; S, 9.30. Found: C, 66.25; H, 6.26; N, 8.22; S, 9.04.

EXAMPLE 38:
4-Ethylaminomethyl-9-phenyl-2,3,4,9-tetrahydrothiopyrano[2,3-b]indole To a solution of 4-formyl-9-phenyl-2,3,4,9-tetrahydro[2,3-b]indole (1.8 g) in benzene (20 ml) is added a solution of ethylamine (690 mg) in ethanol (3.4 ml). The mixture is stirred at room temperature for 2 hours and evaporated. The residue is treated in the same manner as in Example 330 to give the hydrochloride (1.3 g) of the title compound melting at 232°–238° C. (decomp.).

NMR: $\delta_{CDCl_3}$ 1.13t(7)3H, 1.77brs1H, 2.77q(7)2H, 7.43s5H (free base).

Anal. Calcd. for $C_{20}H_{22}N_2SCl$:
C, 66.93; H, 6.46; N, 7.80; S, 8.93. Found: C, 66.90; H, 6.09; N, 7.52; S, 8.97.

EXAMPLE 39:
9-(p-Chlorobenzoyl)-4-methylaminomethyl-2,3,4,9-tetrahydrothiopyrano[2,3-b]indole (1)

4-(N-t-Butoxycarbonyl-N-methylaminomethyl)2,3,4,9-tetrahydrothiopyrano[2,3-b]indole To a solution of 4-methylaminomethyl-2,3,4,9-tetrahydrothiopyrano[2,3-b]indole (4.41 g) in tetrahydrofuran (50 ml) are added triethylamine (4 ml) and 2-(t-butoxycarbonylthio)-4,6-dimethylpyrimidine (4.76 g) successively at room temperature. The mixture is stirred at room temperature for 2.5 hours and evaporated to remove the solvent. The residue is extracted with chloroform after addition of water. The extract is washed, dried and evaporated to give crude crystals. Recrystallization from acetone gives the title compound (5.57 g) melting at 220°-222° C. (decomp.).

Yield: 93%.

IR: $\nu_{max}^{CHCl_3}$ 3460, 1675 cm$^{-1}$.

Anal. Calcd. for $C_{18}H_{24}N_2O_4S$: C, 65.03; H, 7.28; N, 8.43; S, 9.64. Found: C, 64.94; H, 7.28; N, 8.32; S, 9.65.

(2)

9-(p-Chlorobenzoyl)-4-methylaminomethyl-2,3,4,9-tetrahydrothiopyrano[2,3-b]indole To a solution of the product (333 mg) of the above (1) in dimethylformamide (8 ml) is added a 50% suspension (58 mg) of sodium hydride in mineral oil. The mixture is stirred at room temperature for 1 hour and further at 40°-50° C. for 30 minutes. After addition of a solution of p-chlorobenzoyl chloride (210 mg) in dimethylformamide (2 ml) under ice-cooling, the mixture is further stirred at room temperature for 2 hours. A 10% aqueous solution of ammonium chloride (10 ml) is added thereto under ice-cooling. The mixture is extracted with chloroform. The extract is washed with an aqueous solution of sodium bicarbonate and water, dried and evaporated to give 4-(N-t-butoxycarbonyl-N-methylaminomethyl)-9-(p-chlorobenzoyl)-2,3,4,9-tetrahydrothiopyrano[2,3-b]indole as an oil (533 mg).

To a solution of the above product (533 mg) in dichloromethane (4 ml) is added trifluoroacetic acid (2 ml) under ice-cooling. The mixture is stirred at room temperature for 2 hours and evaporated to remove the solvent and agent.

The residue is dissolved in chloroform and washed with a cold aqueous solution of potassium carbonate. The chloroform layer is separated, washed with water, dried and evaporated to remove the solvent. The oily residue is treated with oxalic acid in ethanol to give precipitate. The precipitate is filtered, washed with acetone, dissolved in an aqueous solution of potassium carbonate, and extracted with chloroform. The extract is washed with water, dried and evaporated to give the title compound as an oil (300 mg). Yield: 81%

IR: $\nu_{max}^{CHCl_3}$ 1680 cm$^{-1}$. (free base)

Mp. 252°–255° C. (decomp.) (hydrochloride)

Anal. Calcd. for $C_{20}H_{20}N_2OSCl_2$: C, 58.97; H, 4.95; N, 6.88; S, 7.87. Found: C, 58.83; H, 4.91; N, 6.88; S, 8.14.

EXAMPLES 40-64

Compounds I in Table 7 are obtained by the same procedure as an Example 39 (1) and (2) following the scheme below. The physical constants of the intermediate III are shown in Table 6. The IR and NMR spectra are measured with free bases.

TABLE 6

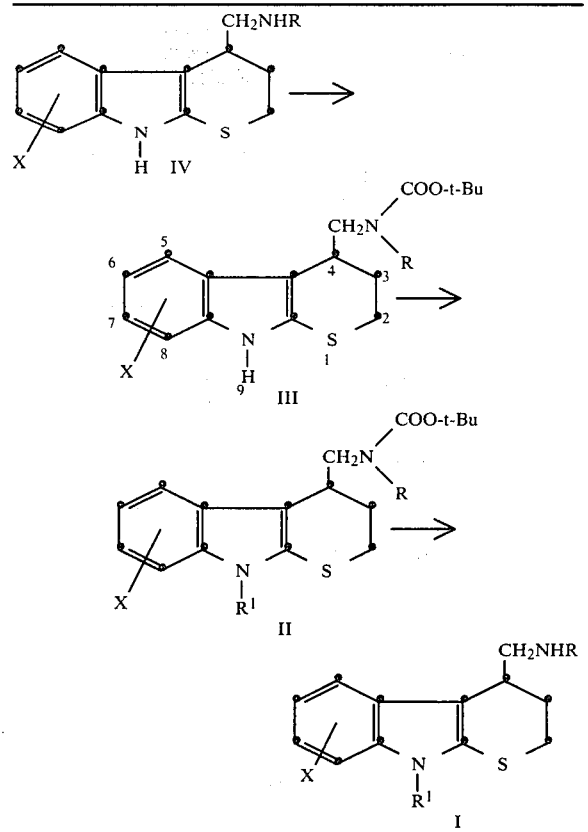

| Compound III | | | Yield |
|---|---|---|---|
| X | R | mp. (°C.) | % |
| 7-CF$_3$ | Me | 185–188 (d) | 85 |
| 6-F | Me | 209–211 | 81 |
| 6-F | Et | 143–145 | 83 |
| 6-F | i-Pr | 145.5–147 | 85 |

Table 7

| | | | | | | | Compound I | | | | | |
|---|---|---|---|---|---|---|---|---|---|---|---|---|
| Ex. No. | X | R | R' | IR: CHCl$_3$ cm$^{-1}$ $\gamma_{max}$ | NMR:$\delta_{CDCl_3}$ | | mp (°C.) | Elemental Analysis: Calcd. Found | | | | Yield (III→I) (%) |
| | | | | | | | | C | H | N | S | |
| 40 | H | Me | Et | —* | 1.32t(7)3H,2.55s 3H,4.06q(7)2H | HCl | 251(d) | C$_{15}$H$_{21}$N$_2$SCl 60.69 60.54 | 7.13 7.11 | 9.44 9.29 | 10.80 10.88 | 67 |
| 41 | H | Me | Pr | — | 0.92t(7)3H,2.47s 3H,3.91t(7)2H | HCl | 246 | C$_{16}$H$_{23}$N$_2$SCl 61.82 61.76 | 7.46 7.52 | 9.01 8.97 | 10.31 10.14 | 64 |
| 42 | H | Me | i-Pr | — | 1.58d(7)6H, 4.58q(7)1H, 2.45s3H | HCl | 243–247 | C$_{16}$H$_{23}$N$_2$SCl 61.82 61.65 | 7.46 7.58 | 9.01 8.74 | 10.31 10.21 | 77 |
| 43 | H | Me | i-Bu | — | 0.92d(7)6H,2.47s 3H,3.80d(7)2H | HCl | 245(d) | C$_{17}$H$_{25}$N$_2$SCl 62.84 62.77 | 7.76 7.84 | 8.62 8.55 | 9.87 10.07 | 66 |
| 44 | H | Me | —⟨H⟩ | — | 2.47s3H | (COOH)$_2$ | 234–237 | C$_{21}$H$_{28}$N$_2$O$_4$S 62.35 62.76 | 6.98 7.06 | 6.92 6.93 | 7.93 8.21 | 20 |
| 45 | H | Me | CH$_2$Ph | — | —** | HCl | 265–276 | C$_{20}$H$_{23}$N$_2$Cl 66.93 66.68 | 6.46 6.48 | 7.80 7.83 | 8.93 8.99 | 72 |
| 46 | H | Me | CH$_2$CH$_2$Ph | — | 2.48s3H, 4.20t(8)2H | HCl | 255–265 | C$_{21}$H$_{25}$N$_2$SCl 67.63 67.85 | 6.76 6.86 | 7.51 7.49 | 8.60 8.61 | 74 |
| 47 | H | Me | CH$_2$CONEt$_2$ | 1660 | 1.13t(7.5)6H,2.45 s3H,3.40q(7.5)4H, 4.75s2H | HCl | 265– | C$_{19}$H$_{28}$N$_3$SOCl 59.75 59.85 C$_{17}$H$_{27}$N$_3$SCl$_2$ | 7.39 7.37 | 11.00 10.96 | 8.39 8.18 | 93 |

Table 7-continued

Compound I

| Ex. No. | X | R | R' | IR: $CHCl_3$ $\gamma_{max}$ $cm^{-1}$ | NMR: $\delta_{CDCl_3}$ | | mp (°C.) | Elemental Analysis: Calcd. Found C H N S | | | | Yield (III→I) (%) |
|---|---|---|---|---|---|---|---|---|---|---|---|---|
| 48 | H | Me | $CH_2CH_2NMe_2$ | — | 2.33s6H, 2.46s3H, 4.13t(8)2H | 2HCl | 252–260 | 54.25 54.23 $C_{15}H_{19}N_2OCl$ | 7.23 7.52 | 11.16 10.80 | 8.52 8.37 | 89 |
| 49 | H | Me | $COCH_3$ | 1695 | 2.46s3H, 2.75s3H | HCl | 256–260(d) | 57.96 57.86 $C_{16}H_{21}N_2OSCl$ | 6.16 6.25 | 9.01 9.00 | 10.32 10.52 | 90 |
| 50 | H | Me | COEt | 1690 | 1.33t(6.5)3H, 2.49 s3H, 3.07q(6.5)2H, 4.5brs1H, 7.1–7.9m | HCl | 250–260(d) | 59.15 58.91 $C_{17}H_{23}N_2OSCl$ | 6.52 6.53 | 8.62 8.55 | 9.87 10.15 | 65 |
| 51 | H | Me | CO—Pr | 1680 | 1.09t(7)3H, | HCl | 221–227(d) | 60.25 59.98 $C_{22}H_{22}N_2O_5S$ | 6.84 6.87 | 8.27 8.16 | 9.46 9.47 | 65 |
| 52 | H | Me | COPh | 1680 | 2.53s3H | $(COOH)_2$ | 236–238(d) | 61.96 61.68 $C_{15}H_{19}N_2O_2SCl$ | 5.20 5.32 | 6.57 6.52 | 7.52 7.77 | 91 |
| 53 | H | Me | COOMe | 1730, 1690 | 2.44s3H, 4.00s3H, 7.0–7.5m3H, 7.8–8.1m1H | HCl | 202–204(d) | 55.12 55.13 $C_{14}H_{18}ClFN_2S$ | 5.86 5.87 | 8.57 8.57 | 9.81 9.92 | 40 |
| 54 | 6-F | Me | Me | — | 2.53s3H, 3.63s3H | HCl | 265–271(d) | 55.90 56.12 $C_{15}H_{20}ClFN_2S$ | 6.03 6.28 | 9.31 9.38 | | 78 |
| 55 | 6-F | Me | Et | — | 2.57s3H, 1.32t(7) 3H | HCl | 253–259(d) | 57.22 57.28 $C_{16}H_{22}ClFN_2S$ | 6.40 6.53 | 8.90 8.99 | | 83.7 |
| 56 | 6-F | Me | i-Pr | — | 1.58d(7)6H, 2.60s 3H, 4.57m(7)1H | HCl | 263–266(d) | 58.43 58.37 $C_{15}H_{18}ClFN_2OS$ | 6.74 6.86 | 8.52 8.70 | | 78.7 |
| 57 | 6-F | Me | COMe | 1690 | 2.43s3H, 2.70s3H | HCl | 252–256(d) | 54.79 54.54 $C_{16}H_{20}ClFN_2SO$ | 5.52 5.50 | 8.52 8.53 | | 73.3 |
| 58 | 6-F | Me | COEt | 1690 | 2.54s3H, 1.37t(7)3H | HCl | 246–250.5(d) | 56.05 55.91 $C_{15}H_{20}FClN_2S$ | 5.88 6.05 | 8.17 8.06 | | 71.8 |
| 59 | 6-F | Et | Me | — | 3.57s3H, 1.10t(7)3H | HCl | 240–246(d) | 57.22 57.31 $C_{16}H_{22}ClFN_2S$ | 6.40 6.47 | 8.90 8.75 | | 87.5 |
| 60 | 6-F | i-Pr | Me | — | 3.58s3H, 1.38d3H, 1.42d(6)3H | HCl | 208–211(d) | 58.43 58.25 $C_{16}H_{17}F_3N_2OS \cdot HCl$ | 6.74 6.69 | 8.52 8.42 | | 81 |
| 61 | 7-$CF_3$ | Me | COMe | 1700 | 2.57s3H, 2.82s3H | HCl | 246–253(d) | 50.73 50.98 $C_{19}H_{21}F_3N_2O_5S$ | 4.79 4.74 | 7.39 7.35 | | 89.2 |
| 62 | 7-$CF_3$ | Me | COEt | 1700 | 2.50s3H, 1.33t(7)3H | $(COOH)_2$ | 258–260(d) | 51.12 50.90 $C_{23}H_{21}F_3N_2OS \cdot HCl$ | 4.74 4.90 | 6.27 6.21 | | 91.6 |
| 63 | 7-$CF_3$ | Me | COCH= CHPh | OS · HCl 1650, 975 | 2.53s3H, 9.89d(16) | HCl | 250–254(d) | 59.16 59.04 $C_{18}H_{19}F_3N_2OS \cdot HCl$ | 4.75 5.04 | 6.00 5.97 | | 91.1 |
| 64 | 7-$CF_3$ | Me | COCH= $CHCH_3$ | 1685, 1650, 965 | 2.51s3H, | HCl | 153–157 | 53.40 53.14 | 4.98 5.08 | 6.92 6.71 | | 72.0 |

*no characteristic absordance
**not measurable for the insolubility

EXAMPLE 65:
7-Trifluoromethyl-4-methylaminomethyl-9-(3-dimethylaminopropyl)-2,3,4,9-tetrahydrothiopyrano[2,3-b]indole By the same procedure as in Example 39(2), 7-trifluoromethyl-4-(N-t-butoxycarbonyl-N-methylaminomethyl)-2,3,4,9-tetrahydrothiopyrano[2,3-b]indole (1.5 g) is made to react with 3-bromopropyl chloride followed by the reaction to remove the butoxycarbonyl group to give 9-(3-chloropropyl)-7-trifluoromethyl-4-methylaminomethyl-2,3,4,9-tetrahydrothiopyrano[2,3-b]indole. Ethanol (15 ml) and a 50% aqueous solution of dimethylamine are added to the product. The solution is heated at 90°–95° C. in a sealed-tube for 8 hours and evaporated to remove the solvent. The residue is dissolved in chloroform and extracted with dilute hydrochloric acid. The extract is adjusted to pH 8 with an aqueous solution of sodium hydroxide and extracted with chloroform. The extract is washed with water, dried and condensed to give the title compound (1.28 g).

Yield: 89.2%
NMR: $\delta_{CDCl_3}$ 2.23s6H, 2.52s3H, 4.15t(7)2H
Mp. 196°–212° C. (decomp.) (oxalate)
Anal. Calcd. for $C_{24}H_{30}F_3N_3O_8S$ (moisture absorption 10 μg/min): C, 48.85; H, 5.35; N, 7.43. Found: C, 48.62; H, 5.91; N, 7.30.

EXAMPLE 66:
7-Trifluoromethyl-9-(3-dimethylamino-2-hydroxypropyl)-4-methylaminomethyl-2,3,4,9-tetrahydrothiopyrano[2,3-b]indole (1) In the same manner as in Example 39(2), 7-trifluoromethyl-4-(N-t-butoxycarbonyl-N-methylaminomethyl)-2,3,4,9-tetrahydrothiopyrano[2,3-b]indole (2.8 g) is made to react with epibromohydrin (1.15 g) to give 7-trifluoromethyl-4-(N-t-butoxyarbonyl-N-methylaminomethyl)-9-(2,3-epoxypropyl)-2,3,4,9-tetrahydrothiopyrano[2,3-b]indole (3.10 g).
Yield: 97.2%
NMR: $\delta_{CDCl_3}$ 1.48s9H, 2.97s3H (2) To the above product are added ethanol (20 ml) and a 50% aqueous solution (3 g) of dimethylamine. The solution is heated at 95° C. in a sealed-tube for 8 hours and condensed to give 7-trifluoromethyl-4-(N-t-butoxycarbonyl-N-methylaminomethyl)-9-(2-hydroxy-3-dimethylaminopropyl)-2,3,4,9-tetrahydrothiopyrano[2,3-b]indole.
IR: $\nu_{max}^{CHCl_3}$ 1680 cm$^{-1}$
NMR: $\delta_{CDCl_3}$ 1.48s9H, 2.22s6H, 2.96s3H (3) The above product is treated with trifluoroacetic acid in the same manner as in Example 39(2) to give the title compound as an oil. The total yield is 94.2%.
IR: $\nu_{max}^{CHCl_3}$ 3300 cm$^{-1}$
NMR: $\delta_{CDCl_3}$ 2.28s6H, 2.45s3H
Mp. 191°-200° C. (decomp.) (oxalate)
Anal. Calcd. for $C_{23}H_{30}F_3N_3O_9S$: C, 47.14; H, 5.42; N, 7.28. Found: C, 47.29; H, 5.48; N, 6.92.

EXAMPLE 67:
7-Trifluoromethyl-9-(2-hydroxy-3-propylaminopropyl)-4-methylaminomethyl-2,3,4,9-tetrahydrothiopyrano[2,3-b]indole The same procedure as in Example 66 using the same starting compound and propylamine instead of dimethylamine in step (2) gives the title compound through the following compound. Total yield: 80.1%
7-Trifluoromethyl-4-(N-t-butoxycarbonyl-N-methylaminomethyl)-9-(2-hydroxy-3-propylaminopropyl)-2,3,4,9-tetrahydrothiopyrano[2,3-b]indole
NMR: $\delta_{CDCl_3}$ 0.99d(6)6H, 1.48s9H, 2.96s3H
Physical constants of the title compound:
IR: $\nu_{max}^{CHCl_3}$ 3000, 1370 cm$^{-1}$
NMR: $\delta_{CDCl_3}$ 1.00d(6)6H, 2.40s3H
Mp. 205°-210° C. (decomp.) (oxalate)
Anal. Calcd. for $C_{24}H_{32}F_3N_3O_9S$: C, 48.40; H, 5.42; N, 7.06 Found: C, 48.22; H, 5.70; N, 6.78

EXAMPLE 68:
8-Ethyl-9-cyclopropylmethyl-4-methylaminomethyl-2,3,4,9-tetrahydrothiopyrano[2,3-b]indole (1)
8-Ethyl-4-(N-methyl-N-trifluoroacetylaminomethyl)-2,3,4,9-tetrahydrothiopyrano[2,3-b]indole To a solution of 8-ethyl-4-methylaminomethyl-2,3,4,9-tetrahydrothiopyrano[2,3-b]indole (2.60 g) in methylene chloride (30 ml) is added pyridine (3 ml) and a solution of trifluoroacetic anhydride (2.73 g) in methylene chloride (3 ml) is added dropwise under ice cooling. The mixture is stirred for 2 hours and extracted with methylene chloride under ice-cooling after addition of water. The extract is washed with water, dried and evaporated to give an oily residue (3.5 g). The product is purified by column chromatography on silica gel and recrystallized from benzene to give the title compound (3.3 g) melting at 131°-134° C. Yield: 93%
IR: $\nu_{max}^{CHCl_3}$ 3460, 1685 cm$^{-1}$
Anal. Calcd. for $C_{17}H_{19}N_2OSF_3$: C, 57.29; H, 5.37 N, 7.86; S, 9.00. Found: C, 57.35; H, 5.31; N, 7.80; S, 9.04.

(2)
8-Ethyl-9-cyclopropylmethyl-4-methylaminomethyl-2,3,4,9-tetrahydrothiopyrano[2,3-b]indole To a solution of the product (1.35 g) of the above (1) in dimethylformamide (15 ml) is added a 50% suspension (255 mg) of sodium hydride in mineral oil. The mixture is heated at 40° C. for 1 hour. A solution of cyclopropylmethyl bromide (767 mg) in dimethylformamide (2 ml) is added thereto at room temperature under stirring. The mixture is stirred at 40° C. for 22 hours and extracted with ether under ice-cooling after addition of ice water (20 ml). The extract is washed with water and evaporated to give an oil (1.53 g). The oil is purified by column chromatography on silica gel to give 8-ethyl-9-cyclopropylmethyl-4-(N-methyl-N-trifluoroacetylaminomethyl)-2,3,4,9-tetrahydrothiopyrano[2,3-b]indole as an oil (1.17 g). Yield: 76%

To a solution of the product (1.16 g) in methanol (10 ml) is added an aqueous solution (2 ml) of sodium hydroxide (266 mg). The solution is stirred at room temperature for 18 hours and evaporated to remove the solvent. After addition of water, the residue is extracted with chloroform. The extract is washed with water, dried and evaporated to give an oil (840 mg). The product is treated with an ethereal solution of hydrogen chloride in acetone to give the hydrochloride (740 mg) of the title compound melting at 261°-266° C.
Yield: 75%
Anal. Calcd. for $C_{19}H_{27}N_2SCl$: C, 65.02; H, 7.75; N, 7.98. Found: C, 65.03; H, 7.51; N, 7.95.

EXAMPLES 69-70

The following compounds are obtained by the same procedure as in Example 68 using the same starting compound and allyl or isopropyl bromide instead of cyclopropylmethyl bromide.
9-Allyl-8-ethyl-4-methylaminomethyl-2,3,4,9-tetrahydrothiopyrano[2,3-b]indole
IR: $\nu_{max}^{CHCl_3}$ 1640, 995, 920 cm$^{-1}$
NMR: $\delta_{CDCl_3}$ 2.43s
Mp. 234°-242° C. (decomp.) (hydrochloride)
Anal. Calcd. for $C_{18}H_{25}ClN_2S$: C, 64.17; H, 7.48; N, 8.31. Found: C, 64.06; H, 7.53; N, 8.23.
9-Isopropyl-8-ethyl-4-methylaminomethyl-2,3,4,9-tetrahydrothiopyrano[2,3-b]indole
IR: $\nu_{max}^{CHCl_3}$ 1370
NMR: $\delta_{CDCl_3}$ 1.62d(7)6H, 2.48s3H, 5.23(7)1H
Mp. 253°-257° C. (decomp.) (hydrochloride)
Anal. Calcd. for $C_{18}H_{27}N_2ClS$: C, 63.79; H, 8.03; N, 8.26 Found: C, 63.68; H, 8.15; N, 8.41

EXAMPLE 71:
9-Methyl-4-methylaminomethyl-2,3,4,9-tetrahydrothiopyrano[2,3-b]indole A solution of 4-methylaminomethyl-2,3,4,9-tetrahydrothiopyrano[2,3-b]indole (1.63 g) in tetrahyfrofuran (5 ml) is added dropwise to a solution of sodium amide in liquid ammonia prepared from sodium (193 mg) and liquid ammonia (100 ml) and after 5 minutes, a solution of methyl iodide (1.20 g) in tetrahydrofuran (5 ml). The mixture is stirred for 1 hour and evaporated to remove the liquid ammonia after addition of ammonium chloride (150 mg). After addition of water, the residue is extracted with ether. The extract is washed, dried and evaporated. The residue (1.7 g) is dissolved in methanol and treated with oxalic acid to give the oxalate (2.1 g) of the title compound melting at 251°-254° C. (decomp.)
Yield: 89%
Anal. Calcd. for $C_{16}H_{20}O_4N_2S$: C, 57.13; H, 5.99; N, 8.33; S, 9.53. Found: C, 57.08; H, 6.04; N, 8.04; S, 9.77.

EXAMPLE 72:
9-Acetyl-4-dimethylaminoethyl-2,3,4,9-tetrahydrothiopyrano[2,3-b]indole To a solution of 4-dimethylaminomethyl-2,3,4,9-tetrahydrothiopyrano[2,3-b]indole (246 mg) in dimethylformamide (4 ml) is added a 50% suspension (72 mg) of sodium hydride in mineral oil. The mixture is stirred at 40° C. for 30 minutes and further at room temperature for 1 hour after addition of acetyl chloride (95 mg) under ice-cooling and a cold aqueous solution of ammonium chloride is added thereto followed by extraction with chloroform. The extract is washed with water, dried and evaporated. The residue is washed with pentane to give crystals of the title compound (244 mg) melting at 131°–133° C. Yield: 84%

IR: $\nu_{max}^{CHCl_3}$ 1695 cm$^{-1}$

Anal. Calcd. for $C_{16}H_{20}N_2OS$: C, 66.63; H, 6.99; N, 9.71; S, 11.21. Found: C, 66.73; H, 7.07; N, 9.52; S, 10.91.

Mp. 225°–232° C. (decomp.) (hydrochloride)

EXAMPLES 73–74

The same procedure as in Example 72 gives the following compounds:

9-Methyl-4-dimethylaminomethyl-2,3,4,9-tetrahydrothiopyrano[2,3-b]indole (Yield: 93%, oil)

NMR: $\delta_{CDCl_3}$ 2.33s6H, 3.59s3H

Mp. 234°–236° C. (decomp.) (oxalate)

Anal. Calcd. for $C_{17}H_{22}O_4N_2S$: C, 58.26; H, 6.33; N, 8.00 Found: C, 58.10; H, 6.23; N, 8.15

9-(p-Chlorobenzyl)-4-dimethylaminomethyl-2,3,4,9-tetrahydrothiopyrano[2,3-b]indole (Yield: 61%, oil)

IR: $\nu_{max}^{CHCl_3}$ 1680 cm$^{-1}$

Mp: 201°–203° C. (decomp.) (oxalate)

Anal. Calcd. for $C_{23}H_{23}ClN_2O_5S$: C, 58.16; H, 4.88; N, 5.90.

Found: C, 57.98; H, 4.80; N, 5.73.

EXAMPLE 75:
9-Hydroxymethyl-4-dimethylaminomethyl-2,3,4,9-tetrahydrothiopyrano[2,3-b]indole To a solution of 4-dimethylaminoethyl-2,3,4,9-tetrahydrothiopyrano[2,3-b]indole (1.76 g) in tetrahydrofuran (25 ml) are added 37% formalin (8 ml) and a 20% aqueous solution (1.2 ml) of potassium carbonate. The mixture is stirred at room temperature for 2.5 hours and evaporated to remove the solvent partly. Ether is added to the residue. The ether layer is separated, washed with a saline solution, dried and evaporated to give an oil (2.1 g). Recrystallization from ethyl acetate gives the title compound as colorless needles (1.24 g) melting at 129°–130° C. Yield: 84%

EXAMPLE 76:
4-(N-Benzyl-N-methylaminomethyl)-2,3,4,9-tetrahydrothiopyrano[2,3-b]indole To a solution of 4-benzylaminomethyl-2,3,4,9-tetrahydrothiopyrano[2,3-b]indole (1.39 g) in tetrahydrofuran (30 ml) are added acetic acid (1.2 ml), 37% formalin (3.4 ml) and sodium cyanoborohydride (793 mg) successively. The mixture is stirred at room temperature for 1 hour and evaporated to remove the solvent. After addition of some pieces of ice and a 10% aqueous solution of sodium hydroxide, the residue is extracted with ether. The extract is washed with water, dried and evaporated to give an oil (1.48 g). The oil is chromatographed on a column of basic alumina (containing 3% water, 40 g) and eluted with benzene. The eluate is condensed to give the title compound (950 mg) melting at 91°–93° C.

IR: $\nu_{max}^{CHCl_3}$ 3470 cm$^{-1}$

Anal. Cald. for $C_{20}H_{22}N_2S$: C, 74.49; H, 6.88; N, 8.69. Found: C, 74.38; H, 6.96; N, 8.45.

EXAMPLE 77:
4-(N-Isopropyl-N-methylaminomethyl)-2,3,4,9-tetrahydrothiopyrano[2,3-b]indole The title compound is prepared by the same procedure as in Example 76 with 4-isopropylaminomethyl-2,3,4,9-tetrahydrothiopyrano[2,3-b]indole (1.42 g) as a starting compound. Recrystallization from ethyl acetate-petroleum benzine gives colorless needless melting at 116°–118° C.

IR: $\nu_{max}^{CHCl_3}$ 3450 cm$^{-1}$

NMR: $\delta_{CDCl_3}$ 0.97d(6.5)3H, 1.01d(6.5)3H, 2.38s3H, 7.70brs1H

Anal. Calcd. for $C_{16}H_{22}N_2S$: C, 70.02; H, 8.08; N, 10.20. Found: C, 70.23; H, 8.04; N, 10.05.

EXAMPLE 78:
4-(2-Aminoethyl)-2,3,4,9-tetrahydrothiopyroano[2,3-b]indole (1)

Ethyl-2,3,4,9-tetrahydrothiopyrano[2,3-b]indolyl-4-cyanoacetate

A solution of 2-propargylthioindole (1.93 g) in a mixture of ethanol (20 ml) and triethylamine (0.1 ml) is refluxed for 1.5 hours and further 4 hours after addition of ethyl cyanoacetate (2.33 g) and triethylamine (2 ml) and evaporated.

The residue is purified by chromatography on column of silica gel to give the title compound as white crystals (730 mg) melting at 136°–138° C. Yield: 24%.

IR: $\nu_{max}^{CHCl_3}$ 3450, 2240, 1730 cm$^{-1}$

NMR: $\delta_{CDCl_3}$ 1.26t(7)3H, 4.21d(5)1H, 4.23q(7)2H

Anal. Calcd. for $C_{16}H_{16}O_2N_2S$: C, 63.97; H, 5.37; N, 9.34; S, 10.67. Found: C, 63.97; H, 5.38; N, 9.24; S, 10.88

(2)

4-Cyanomethyl-2,3,4,9-tetrahydrothiopyrano[2,3-b]indole

The product of the above (1) is dissolved in a mixture of ethanol (16 ml) and water (4 ml) and potassium carbonate (552 mg) is added thereto.

The mixture is refluxed for 1.5 hours, adjusted near pH 1 with conc. hydrochloric acid and extracted with ether. The extract is condensed to give 2-cyano-2-(2,3,4,9-tetrahydrothiopyrano[2,3-b]indole-4-yl)acetic acid as an oil.

The product is dissolved in quinoline (5 ml), heated at 170° C. for 2 hours and extracted with ether. The extract is condensed. The residue is purified by chromatography on silica gel to give the title compound as white crystals (301 mg) melting at 94°–98° C.

IR: $\nu_{max}^{CHCl_3}$ 3460, 2240 cm$^{-1}$

Anal. Calcd. for $C_{13}H_{12}NS$: C, 68.38; H, 5.32; N, 12.27; S, 14.04. Found: C, 68.36; H, 5.17; N, 12.01; S, 14.11.

(3)

4-(2-Aminoethyl)-2,3,4,9-tetrahydrothiopyrano[2,3-b]indole

A suspension of the product of the above (2) (1.40 g) in ether (40 ml) is added dropwise to a suspension of lithium aluminium hydride (467 mg) and aluminium chloride (1.63 g) in ether. The mixture is stirred at room temperature for 2.5 hours and extracted with ether-ethyl acetate after addition of an aqueous solution of sodium hydroxide. The extract is condensed. The residue is crystallized from ethyl acetate-methanol to give the title compound as white crystals (1.13 g) melting at 136°–138° C. Yield: 79%.

IR: $\nu_{max}^{CHCl_3}$ 3450 cm$^{-1}$

Anal. Calcd. for $C_{13}H_{16}N_2S$: C, 67.20; H, 6.94; N, 12.06; S, 13.80. Found: C, 67.11; H, 7.04; N, 11.82; S, 13.76.

EXAMPLE 79:
4,9-Dimethyl-4-methylaminomethyl-2,3,4,9-tetrahydrothiopyrano[2,3-b]indole (1)

4-Formyl-4,9-dimethyl-2,3,4,9-tetrahydrothiopyrano[2,3-b]indole

To a 50% aqueous solution of sodium hydroxide (12 g) are added tetrabutylammonium bromide (900 mg) and chloroform (18 ml) successively. The solution is stirred at room temperature and a mixture of 4-formyl-2,3,4,9-tetrahydrothiopyrano[2,3-b]indole (3.0 g), chloroform (4 ml) and methyl iodide (12 g) is added thereto at a time.

The solution is stirred at room temperature for 2 hours and diluted with ether. The organic layer is separated, washed with water, dried and evaporated to remove the solvent. The oily residue (3.85 g) is chromatographed on a column of silica gel eluted with hexane-benzene.

The eluate is evaporated to remove the solvent. Recrystallization of the residue from acetone-petraleum benzine gives the title compound as pale green crystals melting at 89.5°–91.0° C.

Anal. Calcd. for $C_{14}H_{15}NOS$: C, 68.54; H, 6.16; N, 5.71; S, 13.07. Found: C, 68.46; H, 6.15; N, 5.62; S, 12.96.

(2)

4,9-Dimethyl-4-methylaminomethyl-2,3,4,9-tetrahydrothiopyrano[2,3-b]indole

To a solution of the product (2.0 g) of the above (1) in benzene (20 ml) is added a 30% solution (14 ml) of methylamine in methanol. The solution is stirred for 2 hours and evaporated to give 4,9-dimethyl-4-methyliminomethyl-2,3,4,9-tetrahydrothiopyrano[2,3-b]indole (IR: $\nu_{max}^{CHCl_3}$ 1660 cm$^{-1}$). The product is dissolved in methanol (20 ml) and sodium borohydride (930 mg) is added thereto on ice bath. The mixture is stirred at room temperature for 1 hour and evaporated to remove the solvent. The residue is extracted with ether after addition of some pieces of ice and a 10% aqueous solution of sodium hydroxide. The ethereal extract is again extracted with hydrochloric acid. The extract is made alkaline with an aqueous solution of sodium hydroxide and extracted with ether. The extract is washed with a saline solution, dried and evaporated to give an oil. Crystallization from hydrochloric acid—ethanol gives the hydrochloride (2.06 g) of the title compound melting at 274° C. (decomp.). Yield: 86%.

NMR: $\delta_{CDCl_3}$ 0.95brs, 1.41s, 2.33s, 3.56s, 7.1–7.9m

Anal. Calcd. for $C_{15}H_{21}N_2SCl$: C, 60.69; H, 7.13; N, 9.44; S, 10.80. Found: C, 60.40; H, 7.13; N, 9.41; S, 11.00.

EXAMPLE 80:
4-Methylaminomethyl-2,3,4,9-tetrahydrothiopyrano[2,3-b]indole S-oxide To a solution of 4-methylaminomethyl-2,3,4,9-tetrahydrothiopyrano[2,3-b]indole (1.26 g) in methanol (40 ml) is added an aqueous solution (20 ml) of sodium metaperiodate (1.32 g) at room temperature. The mixture is stirred at room temperature for 4 hours. The precipitated crystals of sodium iodide are filtered off. The filtrate is condensed and extracted with chloroform after addition of an aqueous solution of potassium carbonate.

The extract is washed with water, dried and evaporated to give an oil. The oil is treated with a solution of oxalic acid in methanol to give crystals. Recrystallization from water gives the oxalate (1.49 g) of the title compound melting at 194°–198° C. (decomp.). Yield: 83%

IR: $\nu_{max}^{CHCl_3}$ 3540, 1010 cm$^{-1}$ (free base)

NMR: $\delta_{CDCl_3}$ 2.48s3H (free base)

Anal. Calcd. for $C_{15}H_{18}N_2O_5S \cdot \frac{1}{2}H_2O$: C, 51.89; H, 5.51; N, 8.07; S, 9.23. Found: C, 51.69; H, 5.61; N, 7.96; S, 9.29.

EXAMPLE 81:
4-Methylaminomethyl-2,3,4,9-tetrahydrothiopyrano[2,3-b]indole S-dioxide To a solution of 4-(N-methyl-N-t-butoxycarbonylaminomethyl)-2,3,4,9-tetrahydrothiopyrano[2,3-b]indole (1.99 g) in chloroform (240 ml) is added m-chloroperbenzoic acid (2.33 g). The mixture is stirred at room temperature for 3 hours and chloroform (250 ml) is added thereto. The mixture is washed with a 5% aqueous solution of sodium hydroxide, water and a saturated saline solution, dried and evaporated to give 4-(N-methyl-N-t-butoxycarbonylaminomethyl)-2,3,4,9-tetrahydrothiopyrano[2,3-b]indole S-dioxide as crude crystals (2.4 g).

To the product are added methylene chloride (10 ml) and then trifluoroacetic acid (10 ml) under ice-cooling. The mixture is stirred at room temperature for 2 hours and evaporated to give the trifluoroacetate (3.65 g) of the title compound. The product is treated with a 5% aqueous solution (10 ml) of sodium hydroxide and extracted with chloroform. The extract is washed with a saturated saline solution, dried and evaporated. The residue is crystallized from ethanol to give the title compound (1.35 g) melting at 165°–167° C. Yield: 85%

IR: $\nu_{max}^{CHCl_3}$ 3450, 1300, 1140, 1120 cm$^{-1}$

NMR: $\delta_{CD_3COCD_3}$ 2.47s3H

Anal. Calcd. for $C_{13}H_{16}N_2O_2S$: C, 59.07; H, 6.10; N, 10.60; S, 12.13. Found: C, 59.05; H, 6.28; N, 10.32; S, 11.91.

EXAMPLE 82:
4-(1-Methylaminoethyl)-2,3,4,9-tetrahydrothiopyrano[2,3-b]indole (1)

4-(1-Hydroxyethyl)-2,3,4,9-tetrahydrothiopyrano[2,3-b]indole

Methyl magnesium iodide prepared from reaction of magnesium (2.4 g) and methyl iodide (13.9 g) in absolute ether is dissolved in absolute benzene (50 ml) and a solution of 4-formyl-2,3,4,9-tetrahydrothiopyrano[2,3-b]indole (5.5 g) in absolute benzene (60 ml) is added dropwise thereto during 3 hours. The mixture is stirred at room temperature for 1 hour, poured slowly into an ice water containing ammonium chloride (10 g) and extracted with ether. The extract is evaporated. The oily residue is chromatographed on a column of silica gel and eluted with ether-benzene (1:50). The eluate is evaporated. The residue is again chromatographed on a column of silica gel and eluted with benzene and ether-benzene (1:20). The title compound is obtained from the latter eluate as an oil (4.58 g).

IR: $\nu_{max}^{CHCl_3}$ 3570, 3460 cm$^{-1}$

NMR: $\delta_{CDCl_3}$ 1.17d(6.5)3H, 1.28d(6.5)3H, 1.78brs, 3.9–4.5m1H, 6.9–7.6m4H, 8.0brs.

(2) 4-Acetyl-2,3,4,9-tetrahydrothiopyrano[2,3-b]indole

To a solution of the product (300 mg) of the above (1) in dimethylsulfoxide (5 ml) is added acetic anhydride (0.7 ml). The mixture is stirred at room temperature for 20 hours. The reaction mixture is poured into ice water, made alkaline with ammonium hydroxide and extracted with ether. The extract is washed with water, dried and evaporated to give an oil (450 mg). The oil is chromatographed on a column of silica gel and eluted with hexane-benzene (3:10) and benzene. The title compound is obtained from the latter eluate. Recrystallization from acetone-petroleum benzine gives colorless needles melting at 120.5°–122.5° C.

IR: $\nu_{max}^{CHCl_3}$ 3450, 1705 cm$^{-1}$

NMR: $\delta_{CDCl_3}$ 2.13s3H, 3.0–3.3m2H, 3.93t(6), 6.9–7.4m4H 8.10brs1H

Anal. Calcd. for $C_{13}H_{13}NOS$: C, 67.50; H, 5.06; N, 6.06; S, 13.86. Found: C, 67.39; H, 5.59; N, 5.99; S, 13.89.

(3) 4-(1-Methylaminoethyl)-2,3,4,9-tetrahydrothiopyrano[2,3-b]indole

To a solution of the product (1.70 g) in the above (2) in benzene (36 ml) is added a 30% solution of methylamine in methanol (36 ml). The mixture is heated at 100° C. in a sealed tube for 18 hours and then evaporated to give 4-(1-methyliminoethyl)-2,3,4,9-tetrahydrothiopyrano[2,3-b]indole. The product is dissolved in a mixture of tetrahydrofuran (50 ml) and methanol (50 ml) and sodium borohydride (562 mg) is added thereto with stirring on an ice bath. The mixture is stirred at room temperature for 40 minutes and evaporated. The residue is extracted with ether after addition of some pieces of ice and a 10% aqueous solution of sodium hydroxide. The extract is washed with water, dried and evaporated to give the title compound (1.77 g). Recrystallization from acetone gives colorless prisms melting at 179°–187° C. Yield: 64%.

NMR: $\delta_{pyridine-d_5}$ 1.21d(6)3H, 2.20s3H,

Anal. Calcd. for $C_{14}H_{18}N_2S$: C, 68.25; H, 7.36; N, 11.37; S, 13.01. Found: C, 68.44; H, 7.52; N, 11.34; S, 13.12.

EXAMPLE 83:
4-(1-methylaminoethyl)-9-phenyl-2,3,4,9-tetrahydrothiopyrano[2,3-b]indole The same procedure as in Example 82 gives the title compound from 4-formyl-9-phenyl-2,3,4,9-tetrahydrothiopyrano[2,3-b]indole. The L-tartrate melts at 196°–201° C. (decomp.).

NMR: $\delta_{CDCl_3}$ 1.23(6)3H, 1.40brs1H, 2.27s3H, 7.44s5H (free base) Anal. Calcd. for $C_{24}H_{28}N_2O_6S$: C, 61.00; H, 5.97; N, 5.93; S, 6.79. Found: C, 60.96; H, 5.70; N, 5.83; S, 7.07.

What is claimed is:

1. A compound of the formula:

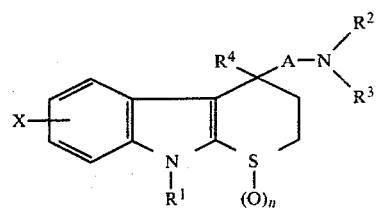

wherein
R$^1$ is hydrogen, C$_{1-6}$ alkyl, hydroxy C$_{1-6}$ alkyl, C$_{2-6}$ alkenyl, phenyl-C$_{1-6}$ alkyl, phenyl, -COR$^5$ wherein R$^5$ is C$_{1-6}$ alkyl, C$_{2-6}$ alkenyl, phenyl or C$_{1-6}$ alkoxy, or R$^1$ is

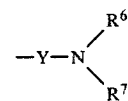

wherein Y is C$_{1-6}$ alkylene, oxo-C$_{1-6}$ alkylene, hydroxy C$_{1-6}$ alkylene and R$^6$ and R$^7$ are each hydrogen or C$_{1-6}$ alkyl;
R$^2$ is hydrogen or C$_{1-6}$ alkyl;
R$^3$ is hydrogen, C$_{1-6}$ alkyl, hydroxy-C$_{1-6}$ alkyl, C$_{2-6}$ alkenyl, phenyl-C$_{1-6}$ alkyl, phenyl or di-C$_{1-6}$ alkyl-amino-C$_{1-6}$ alkyl;
R$^4$ is hydrogen or C$_{1-6}$ alkyl;
A is methylene, C$_{1-6}$ alkyl-methylene, ethylene or C$_{1-6}$ alkylethylene;
X is hydrogen or one or two members selected from the group consisting of halogen, C$_{1-6}$ alkyl, C$_{1-6}$ alkoxy, hydroxy and halogeno-C$_{1-6}$ alkyl; and
n is an integer of 0 to 2,
or a pharmaceutically acceptable salt of said compound.

2. A compound claimed in claim 1 wherein R$^4$ is hydrogen.

3. A compound claimed in claim 2 wherein A is methylene.

4. A compound claimed in claim 2 wherein n is 0.

5. A compound claimed in claim 3 wherein R$^1$ is hydrogen, alkyl, phenyl or —COR$^5$ wherein R$^5$ is C$_{1-6}$ alkyl or phenyl.

6. A compound claimed in claim 5 wherein R$^1$ is hydrogen.

7. A compound claimed in claim 5 wherein R$^1$ is methyl or isopropyl.

8. A compound claimed in claim 5 wherein R$^1$ is acetyl, propionyl or benzoyl.

9. A compound claimed in claim 3 wherein X is hydrogen, methyl, dimethyl, methoxy, dimethoxy, chlorine, fluorine, hydroxy, or trifluoromethyl.

10. A compound claimed in claim 3 wherein X is hydrogen.

11. A compound claimed in claim 3 wherein R$^2$ is hydrogen and R$^3$ is hydrogen or C$_{1-6}$ alkyl.

12. A compound claimed in claim 11 wherein

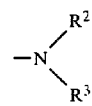

is amino, methylamino, ethylamino or isopropylamino.

13. A compound claimed in claim 12 wherein

is methyamino.

14. The compound claimed in claim 1, namely 4-aminomethyl-2,3,4,9-tetrahydrothiopyrano[2,3-b]indole.

15. The compound claimed in claim 1, namely 4-methylaminomethyl-2,3,4,9-tetrahydrothiopyrano[2,3-b]indole.

16. The compound claimed in claim 1, namely 4-methylaminomethyl-9-methyl-2,3,4,9-tetrahydrothiopyrano[2,3-b]indole.

17. The compound claimed in claim 1, namely 4-methylaminomethyl-2,3,4,9-tetrahydrothiopyrano[2,3-b]indole S-dioxide.

18. The compound claimed in claim 1, namely 4-(N,N-dimethylamino)methyl-9-acetyl-2,3,4,9-tetrahydrothiopyrano[2,3-b]indole.

19. The compound claimed in claim 1, namely 4-methylaminomethyl-9-acetyl-2,3,4,9-tetrahydrothiopyrano[2,3-b]indole.

20. The compound claimed in claim 1, namely 4-methylaminomethyl-9-benzoyl-2,3,4,9-tetrahydrothiopyrano[2,3-b]indole.

21. The compound claimed in claim 1, namely 4-methylaminomethyl-9-isopropyl-2,3,4,9-tetrahydrothiopyrano]2,3-b]indole.

22. The compound claimed in claim 1, namely 4-methylaminomethyl-5,8-dimethyl-2,3,4,9-tetrahydrothiopyrano[2,3-b]indole.

23. The compound claimed in claim 1, namely 4-methylaminomethyl-9-phenyl-2,3,4,9-tetrahydrothiopyrano[2,3-b]indole.

24. The compound claimed in claim 1, namely 4-methylaminomethyl-9-isobutyl-2,3,4,9-tetrahydrothiopyrano[2,3-b]indole.

25. The compound claimed in claim 1, namely 4-methylaminomethyl-9-propionyl-2,3,4,9-tetrahydrothiopyrano[2,3-b]indole.

26. The compound claimed in claim 1, namely 4-methylaminomethyl-9-ethyl-2,3,4,9-tetrahydrothiopyrano[2,3-b]indole.

27. The compound claimed in claim 1, namely 4-methylaminomethyl-9-butyryl-2,3,4,9-tetrahydrothiopyrano[2,3-b]indole.

28. A compound claimed in claim 1 wherein $R^1$ is hydrogen, $C_{1-6}$ alkyl, phenyl or $COR^5$ wherein $R^5$ is $C_{1-6}$ alkyl or phenyl; $NR^2R^3$ is amino, methylamino, ethylamino, isopropylamino or dimethylamino; $R^4$ is hydrogen; A is methylene; X is hydrogen, methyl, dimethyl, methoxy, dimethoxy, chlorine, fluorine, hydroxy, trifluoromethyl; and n is 0.

29. A compound claimed in claim 28 wherein $R^1$ is hydrogen, methyl, isopropyl, acetyl, propionyl or benzoyl; $NR^2R^3$ is amino or methylamino; and X is hydrogen or dimethyl.

* * * * *